United States Patent [19]
Lieb et al.

[11] Patent Number: 6,133,296
[45] Date of Patent: Oct. 17, 2000

[54] SUBSTITUTED PYRIDYL KETO ENOLS

[75] Inventors: Folker Lieb; Hermann Hagemann, both of Leverkusen; Arno Widdig, Odenthal; Michael Ruther; Reiner Fischer, both of Monheim; Thomas Bretschneider, Lohmar; Christoph Erdelen, Leichlingen; Ulrike Wachendorff-Neumann, Neuwied; Alan Graff, Köln; Peter Dahmen, Neuss, all of Germany; Markus Dollinger, Overland, Kans.; Bernd Gallenkamp, Wuppertal, Germany

[73] Assignee: Bayer Aktiengesellschaft, Leverkusen, Germany

[21] Appl. No.: 09/180,118

[22] PCT Filed: Apr. 28, 1997

[86] PCT No.: PCT/EP97/02183

§ 371 Date: Oct. 30, 1998

§ 102(e) Date: Oct. 30, 1998

[87] PCT Pub. No.: WO97/43275

PCT Pub. Date: Nov. 20, 1997

[30] Foreign Application Priority Data

May 10, 1996 [DE] Germany ............... 196 18 831
Dec. 13, 1996 [DE] Germany ............... 196 51 841

[51] Int. Cl.$^7$ ..................... A61K 31/44; C07D 401/00
[52] U.S. Cl. ........................ 514/343; 546/278.7
[58] Field of Search ................ 514/343; 546/278.7

[56] References Cited

U.S. PATENT DOCUMENTS

| | | | |
|---|---|---|---|
| 3,542,809 | 11/1970 | Nakanishi | 260/332.2 |
| 4,678,501 | 7/1987 | Manning | 71/92 |
| 4,837,204 | 6/1989 | Rosenberg et al. | 514/18 |
| 4,985,063 | 1/1991 | Fischer et al. | 71/88 |
| 5,091,537 | 2/1992 | Fischer et al. | 546/226 |
| 5,094,681 | 3/1992 | Kärmer et al. | 71/88 |

(List continued on next page.)

FOREIGN PATENT DOCUMENTS

| | | |
|---|---|---|
| 3314249 | 10/1984 | Germany . |
| 94/01997 | 2/1994 | WIPO . |
| 94/29268 | 12/1994 | WIPO . |
| 95/01358 | 1/1995 | WIPO . |
| 95/20572 | 8/1995 | WIPO . |
| 95/26345 | 10/1995 | WIPO . |

OTHER PUBLICATIONS

Chemical Abstracts 129:28216, Fassler, 1998.
Chemical Abstracts 122:240448, Faessler, 1994.
Chemical Abstracts 122:122443, Hashimoto, 1994.
Chemical Abstracts 119:139787, Faessler, 1993.
Chemical Abstracts 113:132828, Benz, 1990.
Chemical Abstracts 111:168777, Castro, 1988.
Chemical Abstracts 108:205097, Rosenberg, 1987.

(List continued on next page.)

Primary Examiner—D. Margaret Seaman
Attorney, Agent, or Firm—Joseph C. Gil; Carol Marmo

[57] ABSTRACT

The invention relates to new pyridyl-substituted cyclic ketoenols of the formula (I)

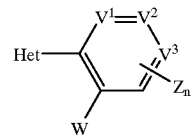

(I)

in which $V^1$, $V^2$ or $V^3$ represents nitrogen,

Het represents one of the groups

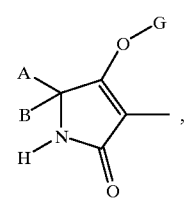

(1)

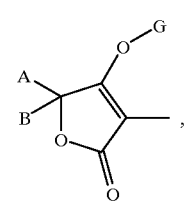

(2)

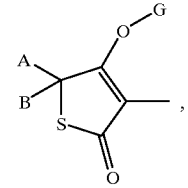

(3)

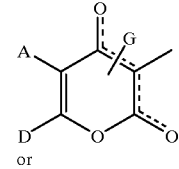

(4)

or

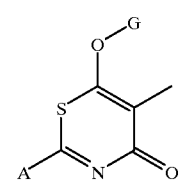

(5)

A, B, G, W, Z and z have the meanings given in the description, to a plurality of processes and intermediates for their preparation, and to their use as pesticides and herbicides.

7 Claims, No Drawings

U.S. PATENT DOCUMENTS

| | | | |
|---|---|---|---|
| 5,116,836 | 5/1992 | Fischer et al. | 514/224.2 |
| 5,142,065 | 8/1992 | Fischer et al. | 548/533 |
| 5,186,737 | 2/1993 | Fischer et al. | 504/283 |
| 5,207,817 | 5/1993 | Krämer et al. | 504/299 |
| 5,225,434 | 7/1993 | Bertram et al. | 514/411 |
| 5,258,527 | 11/1993 | Kraskopf et al. | 548/543 |
| 5,262,383 | 11/1993 | Fischer et al. | 504/195 |
| 5,462,913 | 10/1995 | Fischer et al. | 504/138 |
| 5,494,890 | 2/1996 | Cederbaum et al. | 504/281 |
| 5,504,057 | 4/1996 | Fischer et al. | 504/283 |
| 5,506,193 | 4/1996 | Cederbaum et al. | 504/282 |
| 5,565,450 | 10/1996 | Fischer et al. | 514/227.2 |
| 5,567,671 | 10/1996 | Fischer et al. | 504/283 |
| 5,589,469 | 12/1996 | Fischer et al. | 514/91 |
| 5,602,078 | 2/1997 | Fischer et al. | 504/283 |
| 5,610,122 | 3/1997 | Fischer et al. | 504/251 |
| 5,616,536 | 4/1997 | Fischer et al. | 504/225 |
| 5,622,917 | 4/1997 | Fischer et al. | 504/283 |
| 5,677,449 | 10/1997 | Fischer et al. | 544/165 |
| 5,719,310 | 2/1998 | Fischer et al. | 560/83 |
| 5,830,826 | 11/1998 | Fischer et al. | 504/195 |

OTHER PUBLICATIONS

Chemical Abstracts 105:2066, Castro, 1986.
Chemical Abstracts 104:181191, Castro, 1985.
Chemical Abstracts 101:23356, TenHaken, 1984.
Chemical Abstracts 89:99608, McKennis, 1978.
Chemical Abstracts 86:715, Bowman, 1976.
Chemical Abstracts 84:130204, Wilson, 1976.
Chemical Abstracts 83:644, Bowman, 1975.
Chem Reviews 52, 1953, pp. 234–416.
Bhattacharya, Indian J. Chem. 6, 1968, pp. 341–345.
Chem. Ind. (London) 1968 p. 1568.
Organikum, VEB Deutscher verlag der Wissenschaften, Berlin 1977, p. 507, 517,587.
Organikum 15th edition, p. 533, VEB Deutscher Verlag der Wissenschaften, Berlin 1977.
Ann. Chim, 1970, Paris, 5, p. 11–22–23–27.
L. Munday, J. Chem. Soc. 4372 1961.
J. T. Edward and Chote Jityrangsri, Can J. Chem., 53, 3339, 1975.
M.S. Chambers, E.J. Thomas and D.J. Williams, J. Chem. Soc., Chem. Commun., p. 1228, 1987.
J. Antibiotics 36, No. 11, 1983, p. 1589.
Org. Prep. Procedures Int. 7(4) 155–158, 1975.
Tetrahedron Letters, vol. 27, No. 24, 1986.
Pharmazie 43 1988, H.G. Henning et al, p. 45.
Arch. Pharm. vol. 321, J. Mehnert, 1988, pp. 897–901.
Chem. Abstract. vol. 86, No. 1, Jan. 3, 1977, Abstract No. 715n.
Chem. Abstracts, vol. 109, No. 15, Oct. 10, 1988, Abstract No. 128726c.
Tetrahedron Letters, vol. 29, No. 9, 1988, pp. 971–974.

SUBSTITUTED PYRIDYL KETO ENOLS

The invention relates to new pyridyl-substituted cyclic ketoenols, to a plurality of processes and intermediates for their preparation, and to their use as pesticides and herbicides.

No pyridyl-substituted heterocyclic ketoenols have been described to date. What is known is that certain phenyl-substituted cyclic ketoenols are insecticidally, acaricidally and/or herbicidally active.

Unsubstituted, bicyclic 3-aryl-pyrrolidine-2,4-dione derivatives (EP-A-355 599 and EP-A-415 211) and substituted monocyclic 3-aryl-pyrrolidine-2,4-dione derivatives (EP-A-377 893 and EP-A-442 077) which have a herbicidal, insecticidal or acaricidal action have been disclosed.

Furthermore, polycyclic 3-arylpyrrolidine-2,4-dione derivatives (EP-A 442 073) and 1H-arylpyrrolidinedione derivatives (EP-A-456 063, EP-A-521 334, EP-A-596 298, EP-A-613 884, EP-A-613 885, DE 44 40 594, WO 94/01 997, WO 95/01 358, WO 95/20 572, EP-A-668 267 and WO 95/26 954) have been disclosed.

It has been disclosed that certain substituted $\Delta^3$-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-$\Delta^3$dihydrofuran-2-one) is also described in DE-A-4 014 420. Furthermore, 3-aryl-$\Delta^3$-dihydrofuranone derivatives which have herbicidal, acaricidal and insecticidal properties have been disclosed in EP-A-528 156 and EP-A-0 647 637. 3-Aryl-$\Delta^3$-dihydrothiophenone derivatives have also been disclosed (WO 95/26 345).

Phenyl-pyrone derivatives substituted in the phenyl ring which have herbicidal, acaricidal and insecticidal properties are described in EP-A-588 137.

5-Phenyl-1,3-thiazine derivatives substituted in the phenyl ring which have herbicidal, acaricidal and insecticidal action have been described in WO 94/14 785.

However, the herbicidal, acaricidal and insecticidal activity and/or spectrum of action, and the plant tolerance of these compounds, in particular by crop plants, is not always sufficient.

There have now been found new compounds of the formula (I)

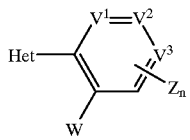

(I)

in which
A) $V^1$ represents nitrogen and
$V^2$ represents CH or C—Z and
$V^3$ represents CY or
B) $V^1$ represents CX and
$V^2$ represents nitrogen and
$V^3$ represents CY or
C) $V^1$ represents CX and
$V^2$ represents CH or C—Z and
$V^3$ represents nitrogen
and in which
W represents hydrogen, cyano, nitro, halogen, alkyl, alkenyl, alkinyl, alkoxy, alkylthio, halogenoalkyl, halogenoalkoxy, halogenoalkenyloxy, or in each case optionally substituted phenyl, phenoxy, phenylthio, phenylalkoxy or phenylalkylthio, X represents hydrogen, halogen, alkyl, alkenyl, alkinyl, alkoxy, alkylthio, halo-genoalkyl, halogenoalkoxy, halogenoalkenyloxy, cyano, nitro or in each case optionally substituted phenyl, phenoxy, phenylthio, phenylalkyloxy or phenylalkylthio, Y represents hydrogen, halogen, alkyl, alkoxy, alkylthio, halogenoalkyl, halo-genoalkoxy, cyano or nitro, Z represents halogen, alkyl, alkoxy, alkylthio, halogenoalkyl, halogenoalkoxy, hydroxyl, cyano, nitro or in each case optionally substituted phenoxy, phenylthio, 5- or 6-membered hetaryloxy, 5- or 6-membered hetarylthio, phenylalkyloxy or phenylalkylthio, or Y and Z together with the carbon atoms to which they are bonded represent an optionally substituted cycle which is optionally interrupted by hetero atoms, in which case n represents 1, or W and Z together with the immediately adjacent carbon atoms to which they are bonded represent an optionally substituted cycle which is optionally interrupted by hetero atoms, in which case n represents 1, n represents 0, 1 or, in the cases A) and C) also 2, it being possible for the substituents Z to be identical or different when n=2, Het represents one of the groups

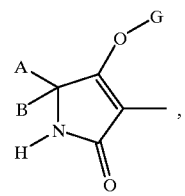

(1)

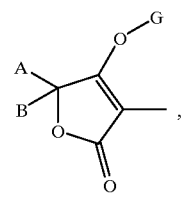

(2)

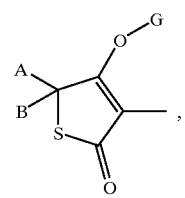

(3)

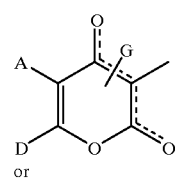

(4)

or

-continued

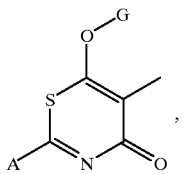
(5)

in which

A represents hydrogen, or represents alkyl, alkenyl, alkoxyalkyl, polyalkoxyalkyl or alkylthioalkyl, each of which is optionally substituted by halogen, or represents in each case saturated or unsaturated and optionally substituted cycloalkyl or heterocyclyl, or represents aryl, arylalkyl or hetaryl, each of which is optionally substituted by halogen, alkyl, halogenoalkyl, alkoxy, halogenoalkoxy, cyano or nitro, B represents hydrogen, alkyl or alkoxyalkyl, or A and B together with the carbon atom to which they are bonded represent a saturated or unsaturated, optionally substituted carbocycle or heterocycle, D represents hydrogen or an optionally substituted radical from the series consisting of alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or A and D together with the atoms to which they are bonded represent an in each case optionally substituted carbocycle or heterocycle, G represents hydrogen (a) or one of the groups

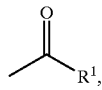
(b)

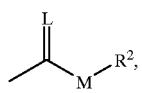
(c)

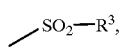
(d)

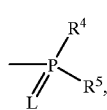
(e)

E or (f)

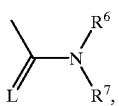
(g)

in which

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is optionally substituted by halogen, or represents cycloalkyl or heterocyclyl, each of which is optionally substituted by halogen, alkyl or alkoxy, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, or represent in each case optionally substituted phenyl, benzyl, phenoxy or phenylthio, $R^6$ and $R^7$ independently of one another represent hydrogen, or represent alkyl cycloalkyl, alkenyl, alkoxy or alkoxyalkyl, each of which is optionally substituted by halogen, or represent in each case optionally substituted phenyl or benzyl, or together with the N atom to which they are bonded form an optionally substituted cycle which optionally contains oxygen or sulphur.

Depending on the nature of the substituents, the compounds of the formula (I) may also be present in the form of geometric and/or optical isomers or variously composed isomer mixtures which, if appropriate, may be separated in the customary manner. The present invention relates to both the pure isomers and the isomer mixtures, to their preparation and use, and to compositions comprising them. In the text which follows, however, compounds of the formula (I) will always be mentioned for the sake of simplicity, even though this is to be understood as meaning the pure compounds or, if appropriate, mixtures comprising various amounts of isomeric compounds.

Depending on whether $V^1$, $V^2$ or $V^3$ represents nitrogen, the compounds of the formula (I) are compounds of the formulae (I-A), (I-B) or (I-C):

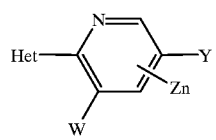
(I-A)

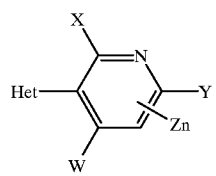
(I-B)

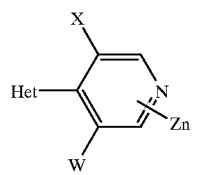
(I-C)

in which

Het, X, Y, Z, W and n have the abovementioned meanings.

To show the position of the pyridyl ring which is occupied by the nitrogen, the text below will occasionally use the letters (A), (B) or (C) when referring to formulae, and also precursors or intermediates.

Taking into consideration the meanings (1) to (5) of the group Het, the following main structures (I-1) to (I-5) result:

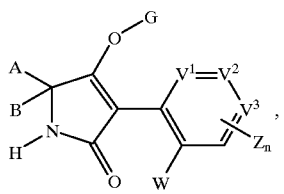
(I-1)
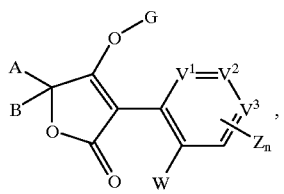
(I-2)
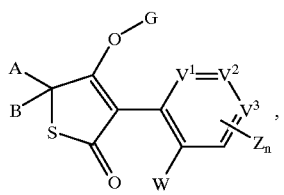
(I-3)
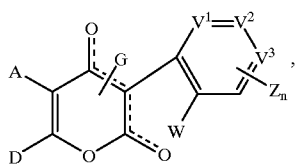
(I-4)
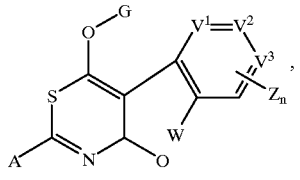
(I-5)
in which
A, B, D, G, W, $V^1$, $V^2$, $V^3$, Z and n have the abovementioned meanings.
Taking into consideration the various meanings (a), (b), (c), (d), (e), (f) and (g) of group G, the following main structures (I-1-a) to (I-1-g) result if Het represents the group (1),
(I-1-a):
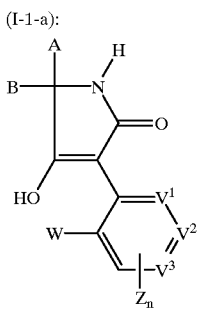
(I-1-b):
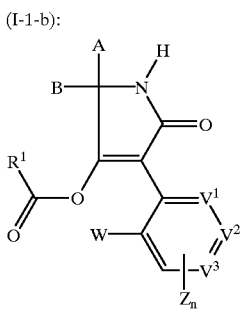
(I-1-c):
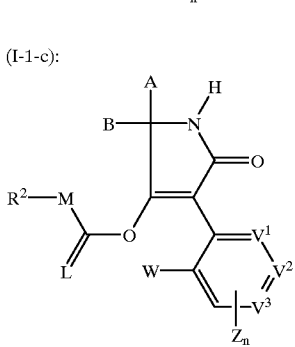
(I-1-d):
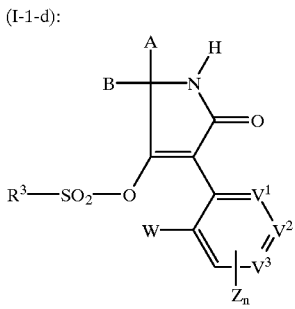
(I-1-e):
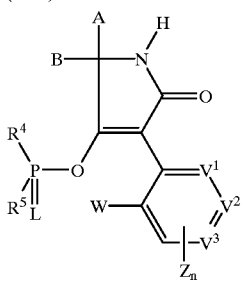

(I-1-f):
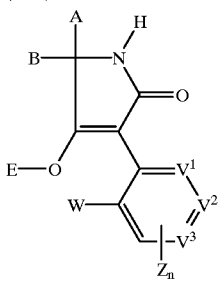

(I-1-g):
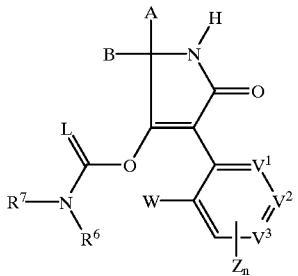

in which

A, B, E, L, M, W, $V^1$, $V^2$, $V^3$, n, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-2-a) to (I-2-g) result if Het represents the group (2):

(I-2-a):
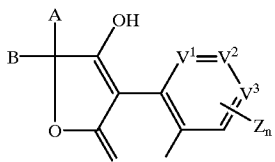

(I-2-b):
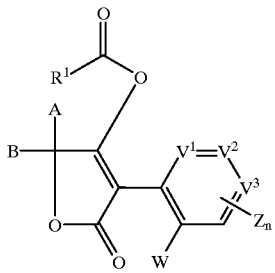

(I-2-c):
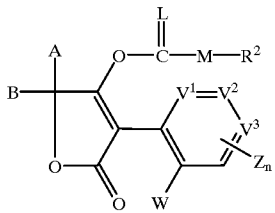

(I-2-d):
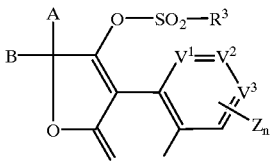

(I-2-e):
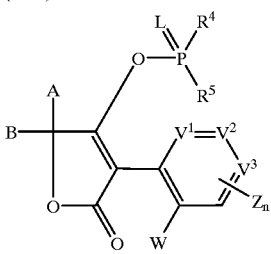

(I-2-f):
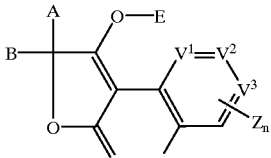

(I-2-g):
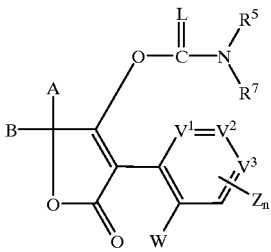

in which

A, B, E, L, M, W, $V^1$, $V^2$, $V^3$, n, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-3-a) to (I-3-g) result if Het represents the group (3):

(1-3-a):
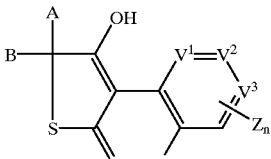

(1-3-b):
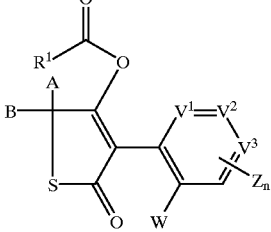

-continued (1-3-c):
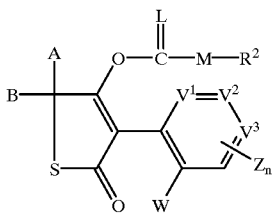

(1-3-d):
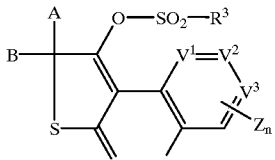

(1-3-e):
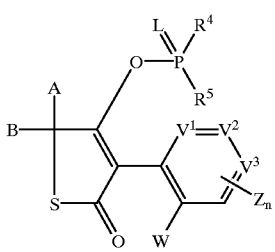

(1-3-f):
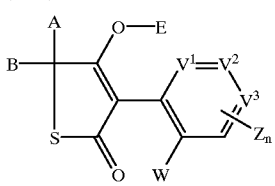

(1-3-g):
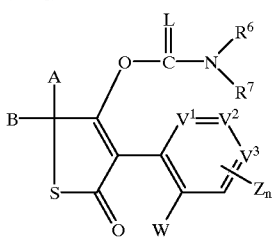

in which

A, B, E, L, M, W, $V^1$, $V^2$, $V^3$, n, Z, $R^1$, $R^2$, $R^3$, $R^4$, $R^5$, $R^6$ and $R^7$ have the abovementioned meanings.

Depending on the position of the substituent G, the compounds of the formula (I-4) may be present in the two isomeric forms of the formulae $(I-4)_a$ and $(I-4)_b$ (I-4)$_a$
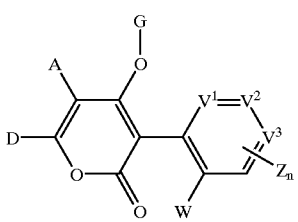

(I-4)$_b$
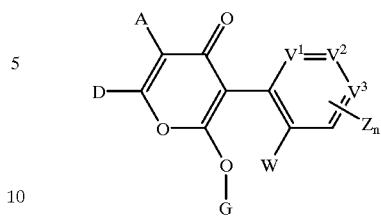

which shall be expressed by the broken line in formula (I-4).

The compounds of the formulae $(I-4)_a$ and $(I-4)_b$ may be present as mixtures, but also in the form of their pure isomers. If desired, mixtures of the compounds of the formulae $(I-4)_a$ and $(I-4)_b$ may be separated by physical methods in a manner known per se, for example by chromatographic methods.

For reasons of clarity, in each case only one of the isomers which are possible will be mentioned in the following text. This does not exclude that, if appropriate, the compounds can be present in the form of the isomer mixtures or in the respective other isomeric form.

Taking, into consideration the various meanings (a), (b), (c), (d), (e), (f) and (g) of group G, the following, main structures (I-4-a) to (I-4-g) result if Het represents the group (4):

(I-4-a):
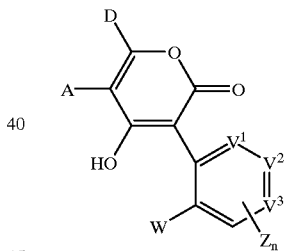

(I-4-b):
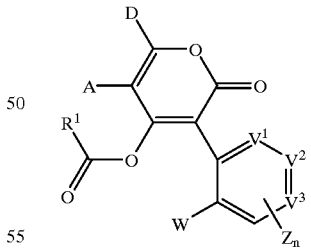

(I-4-c):
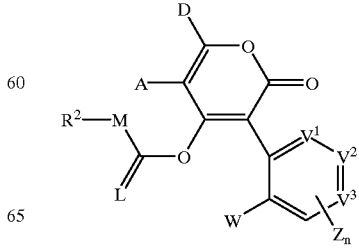

-continued
(I-4-d):
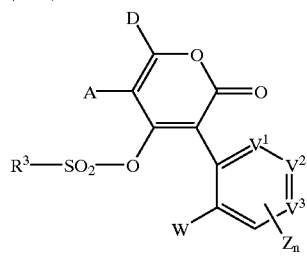
(I-4-e):
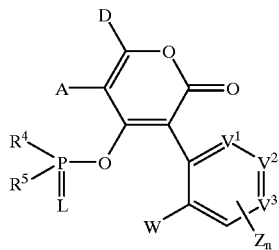
(I-4-f):
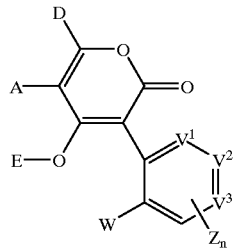
(I-4-g):
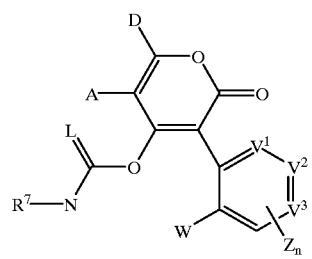
in which
A, D, E, L, M, W, $V^1$, $V^2$, $V^3$, n, Z, $R^1$, $R^2$, $R^3$, $R^4$, $R^5$, $R^6$ and $R^7$ have the abovementioned meanings.
Taking into consideration the various meanings (a), (b), (c), (d), (e), (f) and (g) of group G, the following main structures (I-5-a) to (I-5-g) result if Het represents the group (5):
(I-5-a):
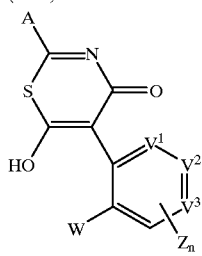
-continued
(I-5-b):
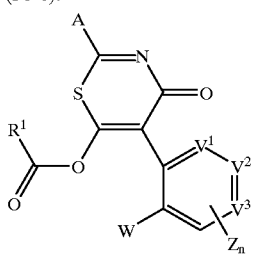
(I-5-c):
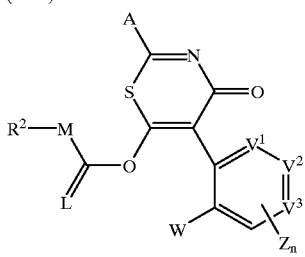
(I-5-d):
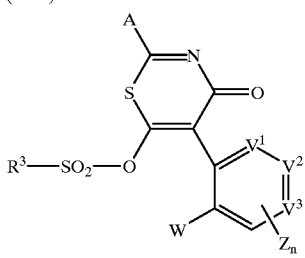
(I-5-e):
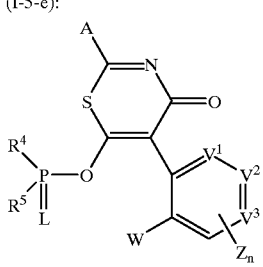
(I-5-f):
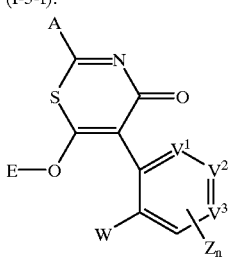
(I-5-g):
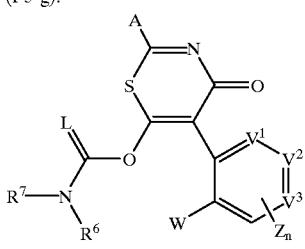

in which

A, E, L, M, W, $V^1$, $V^2$, $V^3$, n, Z, $R^1$, $R^2$, $R^3$, $R^4$, $R^5$, $R^6$ and $R^7$ have the abovementioned meanings.

Furthermore, it has been found that the new compounds of the formula (I) are obtained by the processes described hereinbelow:

(A) Compounds of the formula (I-1-a)

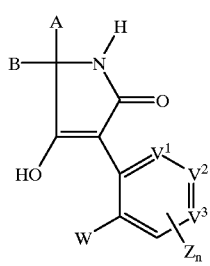
(I-1-a)

in which

A, B, W, $V^1$, $V^2$, $V^3$, n and Z have the abovementioned meanings are obtained when compounds of the formula (II)

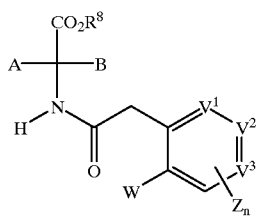
(II)

in which

A, B, W, $V^1$, $V^2$, $V^3$, n and Z have the abovementioned meanings and $R^8$ represents alkyl (preferably $C_1$–$C_6$-alkyl) are subjected to an intramolecular condensation reaction in the presence of a diluent and in the presence of a base.

(B) Furthermore, it has been found that compounds of the formula (I-2-a)

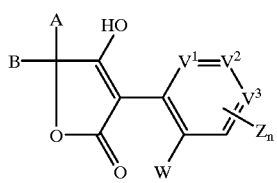
(I-2-a)

in which

A, B, W, $V^1$, $V^2$, $V^3$, n and Z have the abovementioned meanings are obtained when compounds of the formula (III)

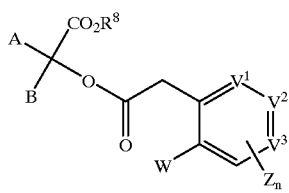
(III)

in which

A, B, W, $V^1$, $V^2$, $V^3$, n, Z and $R^8$ have the abovementioned meanings are subjected to an intramolecular condensation reaction in the presence of a diluent and in the presence of a base.

(C) Moreover, it has been found that compounds of the formula (I-3-a)

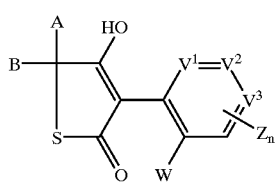
(I-3-a)

in which

A, B, W, $V^1$, $V^2$, $V^3$, n and Z have the abovementioned meanings are obtained when compounds of the formula (IV)

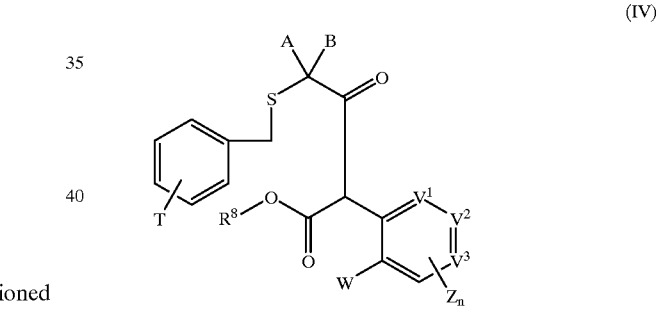
(IV)

in which

A, B, W, $V^1$, $V^2$, $V^3$, n, Z and $R^8$ have the abovementioned meanings and T represents hydrogen, halogen, alkyl (preferably $C_1$–$C_6$-alkyl) or alkoxy (preferably $C_1$–$C_8$-alkoxy) are subjected to an intramolecular cyclization reaction, if appropriate in the presence of a diluent and in the presence of an acid.

(D) Moreover, it has been found that the compounds of the formula (I-4-a)

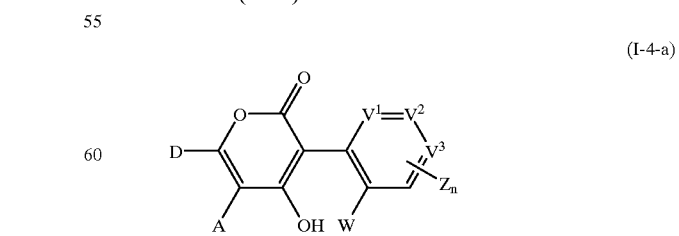
(I-4-a)

in which

A, D, W, $V^1$, $V^2$, $V^3$, n and Z have the abovementioned meanings are obtained when compounds of the formula (V)

(V)

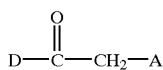

in which

A and D have the abovementioned meanings or their silyl enol ethers of the formula (Va)

(Va)

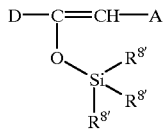

in which

A and D have the abovementioned meanings and $R^{8'}$ represents alkyl (preferably methyl) are reacted with compounds of the formula (VI)

(VI)

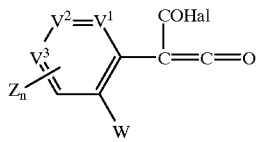

in which

W, $V^1$, $V^2$, $V^3$, n and Z have the abovementioned meanings and Hal represents halogen (preferably chlorine or bromine), if appropriate in the presence of a diluent and if appropriate in the presence of an acid acceptor.

(E) Moreover, it has been found that the compounds of the formula (I-5-a)

(I-5-a)

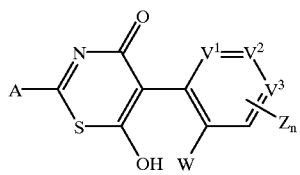

in which

A, W, $V^1$, $V^2$, $V^3$, n and Z have the abovementioned meanings are obtained when compounds of the formula (VII)

(VII)

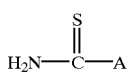

in which

A has the abovementioned meaning are reacted with compounds of the formula (VI)

(VI)

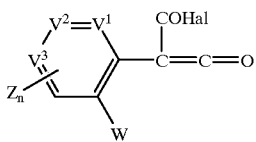

in which

Hal, W, $V^1$, $V^2$, $V^3$, n and Z have the abovementioned meanings, if appropriate in the presence of a diluent and if appropriate in the presence of an acid acceptor.

Furthermore, it has been found (F) that the compounds of the formulae (I-1-b) to (I-5-b) shown above in which A, B, D, $R^1$, W, $V^1$, $V^2$, $V^3$, n and Z have the abovementioned meanings are obtained when compounds of the formulae (I-1-a) to (I-5-a) shown above in which A, B, D, W, $V^1$, $V^2$, $V^3$, n and Z have the abovementioned meanings α) are reacted with acid halides of the formula (VIII)

(VIII)

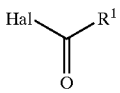

in which $R^1$ has the abovementioned meaning and Hal represents halogen (in particular chlorine or bromine) or β) are reacted with carboxylic anhydrides of the formula (IX)

$R^1$—CO—O—CO—$R^1$      (IX)

in which $R^1$ has the abovementioned meaning, if appropriate in the presence of a diluent and if appropriate in the presence of an acid-binding agent;

(G) that the compounds of the formulae (I-1-c) to (I-5-c) shown above in which A, B, D, $R^2$, W, M, $V^1$, $V^2$, $V^3$, n and Z have the abovementioned meanings and L represents oxygen are obtained when compounds of the formulae (I-1-a) to (I-5-a) shown above in which A, B, D, W, $V^1$, $V^2$, $V^3$, n and Z have the abovementioned meanings are reacted in each case with chloroformic esters or chloroformic thioesters of the formula (X)

$R^2$—M—CO—Cl      (X)

in which $R^2$ and M have the abovementioned meanings, if appropriate in the presence of a diluent and if appropriate in the presence of an acid-binding agent;

(H) that compounds of the formulae (I-1-c) to (I-5-c) shown above in which A, B, D, $R^2$, W, M, $V^1$, $V^2$, $V^3$, n and Z have the abovementioned meanings and L represents sulphur are obtained when compounds of the formulae (I-1-a) to (I-5-a) shown above in which A, B, D, W, $V^1$, $V^2$, $V^3$, n and Z have the abovementioned meanings are reacted in each case α) with chloromonothioformic esters or chlorodithioformic esters of the formula (XI)

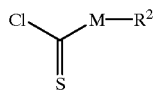

(XI)

in which

M and $R^2$ have the abovementioned meanings, if appropriate in the presence of a diluent and if appropriate in the presence of an acid-binding agent, or β) with carbon disulphide and subsequently with compounds of the formula (XII)

$$R^2\text{-Hal} \quad \text{(XII)}$$

in which $R^2$ has the abovementioned meaning and Hal represents chlorine, bromine or iodine, if appropriate in the presence of a diluent and if appropriate in the presence of a base;

(I) that compounds of the formulae (I-1-d) to (I-5-d) shown above in which A, B, D, $R^3$, W, $V^1$, $V^2$, $V^3$, n and Z have the abovementioned meanings are obtained when compounds of the formulae (I-1-a) to (I-5-a) shown above in which A, B, D, W, $V^1$, $V^2$, $V^3$, n and Z have the abovementioned meanings are reacted in each case with sulphonyl chlorides of the formula (XIII)

$$R^3\text{—}SO_2\text{—}Cl \quad \text{(XIII)}$$

in which $R^3$ has the abovementioned meaning, if appropriate in the presence of a diluent and if appropriate in the presence of an acid-binding agent;

(J) that compounds of the formulae (I-1-e) to (I-5-e) shown above in which A, B, D, L, $R^4$, $R^5$, W, $V^1$, $V^2$, $V^3$, n and Z have the abovementioned meanings are obtained when compounds of the formulae (I-1-a) to (I-5-a) shown above in which A, B, D, W, $V^1$, $V^2$, $V^3$, n and Z have the abovementioned meanings are reacted in each case with phosphorus compounds of the formula (XIV)

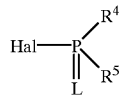

(XIV)

in which

L, $R^4$ and $R^5$ have the abovementioned meanings and Hal represents halogen (in particular chlorine or bromine), if appropriate in the presence of a diluent and if appropriate in the presence of an acid-binding agent;

(K) that compounds of the formulae (I-1-f) to (I-5-f) shown above in which A, B, D, E, W, $V^1$, $V^2$, $V^3$, n and Z have the abovementioned meanings are obtained when compounds of the formulae (I-1-a) to (I-5-a) in which A, B, D, W, $V^1$, $V^2$, $V^3$, n and Z have the abovementioned meanings are reacted in each case with metal compounds or with amines of the formulae (XV) or (XVI)

$$Me(OR^{10})_t \quad \text{(XV)}$$

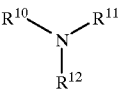

(XVI)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$ and $R^{12}$ independently of one another represent hydrogen or alkyl (preferably $C_1$–$C_8$-alkyl), if appropriate in the presence of a diluent;

(L) that compounds of the formulae (I-1-g) to (I-5-g) shown above in which A, B, D, L, $R^6$, $R^7$, W, $V^1$, $V^2$, $V^3$, n and Z have the abovementioned meanings are obtained when compounds of the formulae (I-1-a) to (I-5-a) shown above in which A, B, D, W, $V^1$, $V^2$, $V^3$, n and Z have the abovementioned meanings are reacted in each case with isocyanates or isothiocyanates of the formula (XVII)

$$R^6\text{—}N\text{=}C\text{=}L \quad \text{(XVII)}$$

in which $R^6$ and L have the abovementioned meanings, if appropriate in the presence of a diluent and if appropriate in the presence of a catalyst, or β) with carbamoyl chlorides or thiocarbamoyl chlorides of the formula (XVIII)

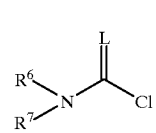

(XVIII)

in which

L, $R^6$ and $R^7$ have the abovementioned meanings, if appropriate in the presence of a diluent and if appropriate in the presence of an acid-binding agent.

Moreover, it has been found that the new compounds of the formula (I) have a very good activity as pesticides, preferably as insecticides, acaricides and herbicides, and are in some cases additionally very well tolerated by plants, in particular crop plants.

The formulae (I) and (I-A), (I-B) and (I-C), respectively, provide general definitions of the compounds according to the invention. Preferred substituents or ranges of the radicals listed in the formulae mentioned hereinabove and hereinbelow are illustrated in the following text:

W preferably represents hydrogen, nitro, cyano, halogen, $C_1$–$C_6$-alkyl, $C_2$–$C_6$-alkenyl, $C_2$–$C_6$-alkinyl, $C_1$–$C_6$-alkoxy, $C_1$–$C_6$-alkylthio, $C_1$–$C_4$-halogenoalkyl, $C_1$–$C_4$-halogenoalkoxy, or represents phenyl, phenoxy, phenylthio, phenyl-$C_1$–$C_4$-alkoxy or phenyl-$C_1$–$C_4$-alkylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

X preferably represents hydrogen, halogen, $C_1$–$C_6$-alkyl, $C_2$–$C_6$-alkenyl, $C_2$–$C_6$-alkinyl, $C_1$–$C_6$-alkoxy, $C_1$–$C_6$-alkylthio, $C_1$–$C_4$-halogenoalkyl, $C_1$–$C_4$-halogenoalkoxy, cyano, nitro, or represents phenyl, phenoxy, phenylthio, phenyl-$C_1$–$C_4$-alkoxy or phenyl-$C_1$–$C_4$-alkylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

Y preferably represents hydrogen, halogen, $C_1$–$C_6$-alkyl, $C_1$–$C_6$-alkoxy, $C_1$–$C_6$-alkylthio, $C_1$–$C_4$-halogenoalkyl, $C_1$–$C_4$-halogenoalkoxy, cyano or nitro.

Z preferably represents halogen, $C_1$–$C_6$-alkyl, $C_1$–$C_6$-alkoxy, $C_1$–$C_6$-alkylthio, $C_1$–$C_4$-halogenoalkyl, $C_1$–$C_4$-halogenoalkoxy, hydroxyl, cyano, nitro, or represents phenoxy, phenylthio, thiazolyloxy, pyridinyloxy, pyrimidyloxy, pyrazolyloxy, phenyl-$C_1$–$C_4$-alkoxy or phenyl-$C_1$–$C_4$-alkylthio, each of which is optionally substituted by halogen, $C_1$–$C_4$-alkyl, $C_1$–$C_4$-alkoxy, $C_1$–$C_4$-halogenoalkyl, $C_1$–$C_4$-halogenoalkoxy, nitro or cyano, or Y and Z preferably together represent $C_3$–$C_4$-alkanediyl, $C_3$–$C_4$-alkenediyl or $C_4$-alkanedienediyl which are in each case optionally substituted by halogen, $C_1$–$C_6$-alkyl, $C_1$–$C_6$-alkoxy or $C_1$–$C_4$-halogenoalkyl and in which one to three members independently of one another can optionally be replaced by oxygen, sulphur, nitrogen or a carbonyl group, in which case n represents 1, or W and Z preferably together represent $C_3$–$C_4$-alkanediyl, $C_{,,}$–$C_4$-alkenediyl or $C_4$-alkanedienediyl which are in each case optionally substituted by halogen, $C_1$–$C_6$-alkyl, $C_1$–$C_6$-alkoxy or $C_1$–$C_4$-halogenoalkyl and in which one to three members independently of one another can optionally be replaced by oxygen, sulphur, nitrogen or a carbonyl group, in which case n represents 1, or n preferably represents 0, 1 or 2, it being possible for the substituents Z to be identical or different if n=2.

Het preferably represents one of the groups

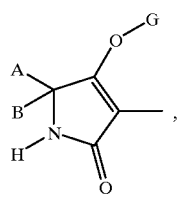

(1)

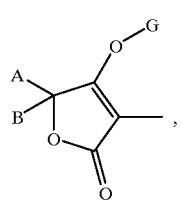

(2)

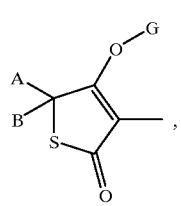

(3)

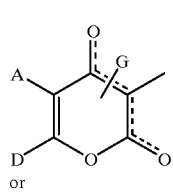

(4)

or

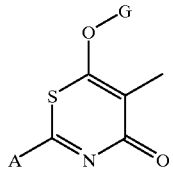

(5)

A preferably represents hydrogen, or represents $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl, naphthyl, phenyl-$C_1$–$C_6$-alkyl, naphthyl-$C_1$–$C_6$-alkyl or hetaryl having 5 or 6 ring atoms and one to three hetero atoms from the series consisting of oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro.

B preferably represents hydrogen, $C_1$–$C_{12}$-alkyl or $C_1$–$C_8$-alkoxy-$C_1$–$C_6$-alkyl, or A, B and the carbon atom to which they are bonded preferably represent $C_3$–$C_{10}$-cycloalkyl or $C_5$–$C_{10}$-cycloalkenyl, in each of which one methylene group is optionally replaced by oxygen or sulphur and which are optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are bonded preferably represent $C_5$–$C_6$-cycloalkyl which is substituted by an alkylenediyl group which optionally contains one or two oxygen and/or sulphur atoms or by an alkylenedioxy group or by an alkylenedithioyl group, this group together with the carbon atom to which it is bonded forming a further five- to eight-membered ring, or A, B and the carbon atom to which they are bonded preferably represent $C_3$–$C_8$-cycloalkyl or $C_5$–$C_8$-cycloalkenyl, in which two carbon atoms are connected by $C_3$–$C_6$-alkanediyl, $C_3$–$C_6$-alkenediyl or $C_4$–$C_6$-alkanedienediyl, each of which is optionally substituted by $C_1$–$C_6$-alkyl, $C_1$–$C_6$-alkoxy or halogen and in each of which one methylene group is optionally replaced by oxygen or sulphur.

D preferably represents hydrogen, or represents $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by halogen, or represents $C_3$–$C_8$-cycloalkyl which is optionally substituted by halogen, $C_1$–$C_4$-alkyl, $C_1$–$C_4$-alkoxy or $C_1$–$C_4$-halogenoalkyl and in each of which one or two methylene groups which are not directly adjacent are replaced by oxygen and/or sulphur, or represents phenyl, hetaryl having 5 or 6 ring atoms and one or two hetero atoms from the series consisting of oxygen, sulphur and nitrogen, phenyl-$C_1$–$C_6$-alkyl or hetaryl-$C_1$–$C_6$-alkyl having 5 or 6 ring atoms and one or two hetero atoms from the series consisting of oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent a $C_3$–$C_6$-alkanediyl, $C_3$–$C_6$-alkenediyl or $C_4$–$C_6$-alkanedienediyl group in each of which one methylene group is optionally replaced by oxygen or sulphur and each of which is optionally substituted by halogen or by $C_1$–$C_{10}$-alkyl, $C_1$–$C_6$-alkoxy, $C_1$–$C_6$-alkylthio, $C_3$–$C_7$-cycloalkyl, phenyl or benzyloxy, each of which is optionally substituted by halogen, or by a further $C_3$–$C_6$-alkanediyl, $C_3$–$C_6$-alkenediyl or $C_4$–$C_6$-alkanedienediyl group which forms a fused ring and in each of which one methylene group is optionally replaced by oxygen or sulphur and which are optionally substituted by $C_1$–$C_6$-alkyl, or A and D together represent a $C_3$–$C_6$-alkanediyl or $C_3$–$C_6$-alkenediyl group, each of which optionally contains one of the following groups

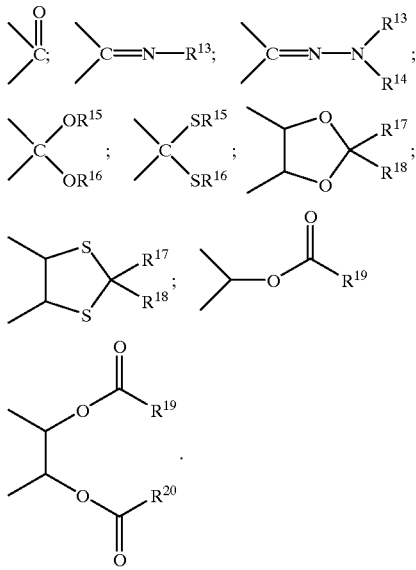

G preferably represents hydrogen (a) or one of the groups (b)

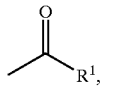

(c)

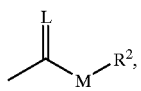

(d)

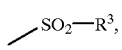

(e)

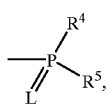

(f)

E or (g)

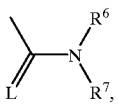

in which
E represents a metal ion equivalent or an ammonium ion,
L represents oxygen or sulphur and M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents 5- or 6-membered hetaryl having one or two hetero atoms from the series consisting of oxygen, sulphur or nitrogen which is optionally substituted by halogen or $C_1$–$C_6$-alkyl, or represents phenoxy-$C_1$–$C_6$-alkyl which is optionally substituted by halogen or $C_1$–$C_6$-alkyl, or represents 5- or 6-membered hetaryloxy-$C_1$–$C_6$-alkyl having one or two hetero atoms from the series consisting of oxygen, sulphur and nitrogen which is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy, or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally substituted by halogen, or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, each of which is optionally substituted by halogen, or represent phenyl or benzyl, each of which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical in which one methylene group is optionally replaced by oxygen or sulphur and which is optionally substituted by $C_1$–$C_6$-alkyl.

$R^{13}$ preferably represents hydrogen, or represents $C_1$–$C_8$-alkyl or $C_1$–$C_8$-alkoxy, each of which is optionally substituted by halogen, or represents $C_3$–$C_8$-cycloalkyl in which one methylene group is optionally replaced by oxygen or sulphur and which is optionally substituted by halogen, $C_1$–$C_4$-alkyl or $C_1$–$C_4$-alkoxy, or represents phenyl, phenyl-$C_1$–$C_4$-alkyl or phenyl-$C_1$–$C_4$-alkoxy, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^{14}$ preferably represents hydrogen or $C_1$–$C_8$-alkyl, or $R^{13}$ and $R^{14}$ together preferably represent $C_4$–$C_6$-alkanediyl.

$R^{15}$ and $R^{16}$ are identical or different and preferably represent $C_1$–$C_6$-alkyl, or $R^{15}$ and $R^{16}$ together preferably represent a $C_2$–$C_4$-alkanediyl radical which is optionally substituted by $C_1$–$C_6$-alkyl or by phenyl which is optionally substituted by halogen, $C_1$–$C_4$-alkyl, $C_1$–$C_4$-halogenoalkyl, $C_1$–$C_4$-alkoxy, $C_1$–$C_4$-halogenoalkoxy, nitro or cyano.

$R^{17}$ and $R^{18}$ independently of one another preferably represent hydrogen, or represent $C_1$–$C_8$-alkyl which is optionally substituted by halogen, or represent phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or $R^{17}$ and $R^{18}$ together with the carbon atom to which they are bonded represent $C_5$–$C_7$-cycloalkyl in which one methylene group is optionally replaced by oxygen or sulphur and which is optionally substituted by $C_1$–$C_4$-alkyl.

$R^{19}$ and $R^{20}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

W especially preferably represents hydrogen, nitro, cyano, fluorine, chlorine, bromine, $C_1$–$C_4$-alkyl, $C_1$–$C_4$-alkoxy, $C_1$–$C_4$-alkylthio, $C_1$–$C_2$-halogenoalkyl, $C_1$–$C_2$-halogenoalkoxy or represents phenyl, phenoxy, benzyl or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

X especially preferably represents hydrogen, fluorine, chlorine, bromine, $C_1$–$C_4$-alkyl, $C_1$–$C_4$-alkoxy, $C_1$–$C_4$-alkylthio, $C_1$–$C_2$-halogenoalkyl, $C_1$–$C_2$-halogenoalkoxy, cyano, nitro, or represents phenyl, phenoxy, benzyl or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

Y especially preferably represents hydrogen, fluorine, chlorine, bromine, $C_1$–$C_4$-alkyl, $C_1$–$C_4$-alkoxy, $C_1$–$C_4$-alkylthio, $C_1$–$C_2$-halogenoalkyl, $C_1$–$C_2$-halogenoalkoxy, cyano or nitro.

Z especially preferably represents fluorine, chlorine, bromine, $C_1$–$C_4$-alkyl, $C_1$–$C_4$-alkoxy, $C_1$–$C_4$-alkylthio, $C_1$–$C_2$-halogenoalkyl, $C_1$–$C_2$-halogenoalkoxy, hydroxyl, cyano, nitro, or represents phenoxy or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

n especially preferably represents 0 or 1.

Het especially preferably represents one of the groups

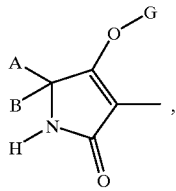
(1)

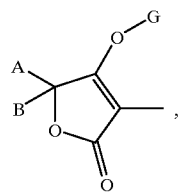
(2)

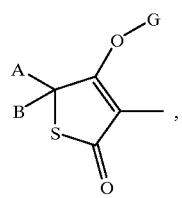
(3)

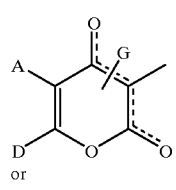
(4)

or

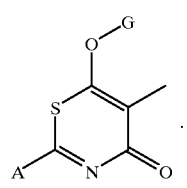
(5)

A especially preferably represents hydrogen, or represents $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or represents $C_3$–$C_7$-cycloalkyl in which one or two methylene groups which are not directly adjacent are optionally replaced by oxygen and/or sulphur and which is optionally substituted by fluorine, chlorine, $C_1$–$C_4$-alkyl or $C_1$–$C_4$-alkoxy, or represents phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B especially preferably represents hydrogen, $C_1$–$C_{10}$-alkyl or $C_1$–$C_6$-alkoxy-$C_1$–$C_4$-alkyl, or A, B and the carbon atom to which they are bonded especially preferably represent $C_3$–$C_8$-cycloalkyl or $C_5$–$C_8$-cycloalkenyl, in each of which one methylene group is optionally replaced by oxygen or sulphur and which are optionally substituted by $C_1$–$C_6$-alkyl or $C_1$–$C_6$-alkoxy, or A, B and the carbon atom to which they are bonded especially preferably represent $C_5$–$C_6$-cycloalkyl which is substituted by an alkylenediyl group which optionally contains one or two oxygen or sulphur atoms or by an alkylenedioxy group or by an alkylenedithioyl group which, together with the carbon atom to which it is bonded, forms a further five- to seven-membered ring, or A, B and the carbon atom to which they are bonded especially preferably represent $C_3$–$C_6$-cycloalkyl or $C_1$–$C_6$-cycloalkenyl in which two carbon atoms are connected by $C_3$–$C_5$-alkanediyl, $C_3$–$C_5$-alkenediyl or butadienediyl, in each of which one methylene group is optionally replaced by oxygen or sulphur and which are optionally substituted by $C_1$–$C_4$-alkyl or $C_1$–$C_4$-alkoxy.

D especially preferably represents hydrogen, or represents $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, or represents $C_3$–$C_7$-cycloalkyl, each of which is optionally substituted by fluorine, chlorine, $C_1$–$C_4$-alkyl, $C_1$–$C_4$-alkoxy or $C_1$–$C_2$-halogenoalkyl and in which one or two methylene groups which are not directly adjacent are optionally replaced by oxygen and/or sulphur, or represents phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together especially preferably represent a $C_3$–$C_5$-alkanediyl or $C_3$–$C_5$-alkenediyl group, in each of which one methylene group is optionally replaced by oxygen or sulphur and which are optionally substituted by fluorine, chlorine or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or each of which optionally contains one of the following groups:

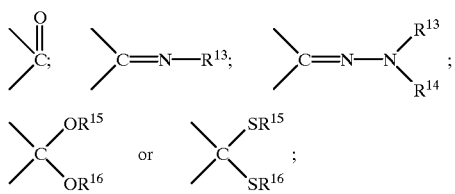

G especially preferably represents hydrogen (a) or one of the groups

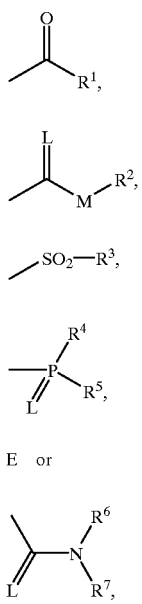

in which
E represents a metal ion equivalent or an ammonium ion,
L represents oxygen or sulphur and
M represents oxygen or sulphur.

$R^1$ especially preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or represents $C_3$–$C_7$-cycloalkyl in which one or two methylene groups which are not directly adjacent are optionally replaced by oxygen and/or sulphur and which is optionally substituted by fluorine, chlorine, $C_1$–$C_5$-alkyl or $C_1$–$C_5$-alkoxy, or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or represents phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyrazolyl, thiazolyl, pyridyl, pyrimidyl, furanyl or thienyl, each of which is optionally substituted by fluorine, chlorine, bromine or $C_1$–$C_4$-alkyl, or represents phenoxy-$C_1$–$C_5$-alkyl which is optionally substituted by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ especially preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, or represents $C_3$–$C_7$-cycloalkyl which is optionally substituted by fluorine, chlorine, $C_1$–$C_4$-alkyl or $C_1$–$C_4$-alkoxy, or represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ especially preferably represents $C_1$–$C_6$-alkyl which is optionally substituted by fluorine or chlorine, or represents phenyl or benzyl, each of which is optionally substituted by fluorine, chlorine, bromine, $C_1$–$C_4$-alkyl, $C_1$–$C_4$-alkoxy, $C_1$–$C_2$-halogenoalkoxy, $C_1$–$C_2$-halogenoalkyl, cyano or nitro.

$R^4$ and $R^5$ independently of one another especially preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another especially preferably represent hydrogen, or represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or represent phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which one methylene group is optionally replaced by oxygen or sulphur.

$R^{13}$ especially preferably represents hydrogen, or represents $C_1$–$C_6$-alkyl or $C_1$–$C_6$-alkoxy, each of which is optionally substituted by fluorine or chlorine, or represents $C_3$–$C_7$-cycloalkyl in which one methylene group is optionally replaced by oxygen or sulphur and which is optionally substituted by fluorine, $C_1$–$C_2$-alkyl or $C_1$–$C_2$-alkoxy, or represents phenyl, phenyl-$C_1$–$C_3$-alkyl or phenyl-$C_1$–$C_2$-alkyloxy, each of which is optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano.

$R^{14}$ especially preferably represents hydrogen or $C_1$–$C_6$-alkyl, or $R^{13}$ and $R^{14}$ together especially preferably represent $C_4$–$C_6$-alkanediyl.

$R^{15}$ and $R^{16}$ are identical or different and represent especially preferably $C_1$–$C_4$-alkyl, or $R^{15}$ and $R^{16}$ together especially preferably represent a $C_2$–$C_3$-alkanediyl radical which is optionally substituted by $C_1$–$C_4$-alkyl or by phenyl which is optionally substituted by fluorine, chlorine, bromine, $C_1$–$C_2$-alkyl, $C_1$–$C_2$-halogenoalkyl, $C_1$–$C_2$-alkoxy, $C_1$–$C_2$-halogenoalkoxy, nitro or cyano.

W very especially preferably represents hydrogen, fluorine, chlorine, bromine, methyl, ethyl, methoxy, ethoxy or trifluoromethyl.

X very especially preferably represents hydrogen, fluorine, chlorine, bromine, methyl, ethyl, methoxy, ethoxy or trifluoromethyl.

Y very especially preferably represents hydrogen, fluorine, chlorine, bromine, methyl, ethyl, methoxy, ethoxy or trifluoromethyl.

Z very especially preferably represents fluorine, chlorine, bromine, methyl, ethyl, methoxy, ethoxy or trifluoromethyl.

n very especially preferably represents 0 or 1.

Het very especially preferably represents one of the groups

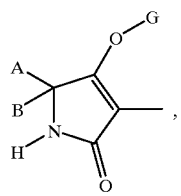

(1)

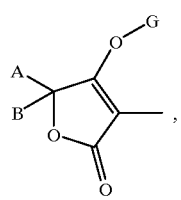

(2)

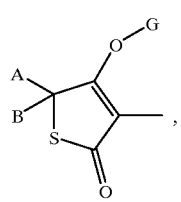

(3)

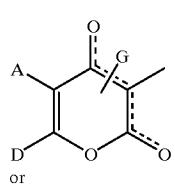

(4)

or

-continued

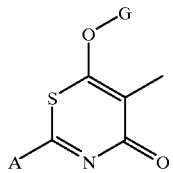

(5)

A very especially preferably represents hydrogen, or represents $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or represents $C_3$–$C_6$-cycloalkyl in which one or two methylene groups which are not directly adjacent are optionally replaced by oxygen and/or sulphur and which is optionally substituted by fluorine, chlorine, methyl or methoxy, or represents phenyl, pyridyl or benzyl, each of which is optionally substituted by fluorine, chlorine, bromine, methyl, ethyl, n-propyl, iso-propyl, methoxy, ethoxy, trifluoromethyl or trifluoromethoxy.

B very especially preferably represents hydrogen, $C_1$–$C_8$-alkyl or $C_1$–$C_4$-alkoxy-$C_1$–$C_2$-alkyl, or A, B and the carbon atom to which they are bonded very especially preferably represent $C_3$–$C_8$-cycloalkyl or $C_5$–$C_8$-cycloalkenyl, in each of which one methylene group is optionally replaced by oxygen or sulphur and which are optionally substituted by methyl, ethyl, n-propyl, iso-propyl, butyl, iso-butyl, sec-butyl, tert-butyl, methoxy, ethoxy, n-propoxy, iso-propoxy, butoxy, iso-butoxy, sec-butoxy or tert-butoxy, or A, B and the carbon atom to which they are bonded very especially preferably represent $C_1$–$C_6$-cycloalkyl which is substituted by an alkylenediyl group which optionally contains an oxygen or sulphur atom or by an alkylenedioxy group, this group together with the carbon atom to which it is bonded forming a further five- to six-membered ring, or A, B and the carbon atom to which they are bonded very especially preferably represent $C_3$–$C_6$-cycloalkyl or $C_5$–$C_6$-cycloalkenyl in which two carbon atoms are connected by $C_3$–$C_4$-alkanediyl, $C_3$–$C_4$-alkenediyl or butadienediyl, in each of which one methylene group is optionally replaced by oxygen or sulphur.

D very especially preferably represents hydrogen, or represents $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl in which one or two methylene groups which are not directly adjacent are optionally replaced by oxygen and/or sulphur and each of which is optionally substituted by fluorine or chlorine, or represents phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together very especially preferably represent a $C_3$–$C_5$-alkanediyl or $C_3$–$C_5$-alkenediyl group, in each of which one methylene group is optionally replaced by oxygen or sulphur and which are optionally substituted by fluorine, chlorine, methyl or methoxy.

G very especially preferably represents hydrogen (a) or one of the groups

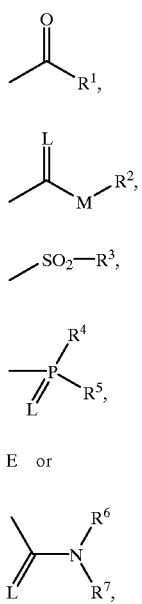

(b)

(c)

(d)

(e)

(f)

E or (g)

in which
E represents a metal ion equivalent or an ammonium ion,
L represents oxygen or sulphur and
M represents oxygen or sulphur.

$R^1$ very especially preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally substituted by fluorine or chlorine, or represents $C_3$–$C_6$-cycloalkyl in which one or two methylene groups which are not directly adjacent are optionally replaced by oxygen and/or sulphur and which is optionally substituted by fluorine, chlorine, methyl, ethyl, n-propyl, i-propyl, n-butyl, i-butyl, tert-butyl, methoxy, ethoxy, n-propoxy or iso-propoxy, or represents phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, or represents benzyl which is optionally substituted by fluorine, chlorine, bromine, methyl, ethyl, n-propyl, i-propyl, methoxy, ethoxy, trifluoromethyl or trifluoromethoxy, or represents furanyl, thienyl or pyridyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very especially preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, or represents $C_3$–$C_6$-cycloalkyl which is optionally substituted by fluorine, chlorine, methyl, ethyl, n-propyl, iso-propyl or methoxy, or is phenyl or benzyl, each of which is optionally substituted by fluorine, chlorine, cyano, nitro, methyl, ethyl, n-propyl, i-propyl, methoxy, ethoxy, trifluoromethyl or trifluoromethoxy, $R^3$ very especially preferably represents methyl, ethyl, propyl, iso-propyl, n-butyl, tert-butyl, each of which is optionally substituted by fluorine or chlorine, or represents phenyl or benzyl, each of which is optionally substituted by fluorine, chlorine, bromine, methyl, ethyl, iso-propyl, tert-butyl, methoxy, ethoxy, iso-propoxy, trifluoromethyl, trifluoromethoxy, cyano or nitro.

$R^4$ and $R^5$ independently of one another very especially preferably represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, methyl, methoxy, trifluoromethyl or trifluoromethoxy.

$R^6$ and $R^7$ independently of one another very especially preferably represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine or chlorine, or represent phenyl or benzyl, each of which is optionally substituted by fluorine, chlorine, bromine, methyl, methoxy or trifluoromethyl, or together represent a $C_5$–$C_6$-alkylene radical in which one methylene group is optionally replaced by oxygen or sulphur and which is optionally substituted by methyl or ethyl.

The rule applies that W and Z together with the carbon atoms to which they are bonded may only then form a ring when these carbon atoms are directly adjacent.

The definitions of radicals or illustrations which have been mentioned above in general or in preferred ranges can be combined with each other as desired, that is to say combinations between the respective ranges and preferred ranges are also possible. They apply to the end products and analogously to the precursors and intermediates.

Preferred according to the invention are those compounds of the formula (I) in which there is a combination of the meanings mentioned above as being preferred (preferable).

Especially preferred according to the invention are those compounds of the formula (I) in which there is a combination of the meanings mentioned above as being especially preferred.

Very especially preferred according to the invention are those compounds of the formula (I) in which there is a combination of the meanings mentioned above as being very especially preferred.

An especially preferred group of compounds of the formula (I) is formed by those in which $V^1$ is nitrogen.

A further especially preferred group of compounds of the formula (I) is formed by those in which $V^2$ is nitrogen.

A further especially preferred group of compounds of the formula (I) is formed by those in which $V^3$ is nitrogen.

Moreover, especially preferred compounds of the formula (I) are those in which G is hydrogen (a) or one of the groups (b)

(c)

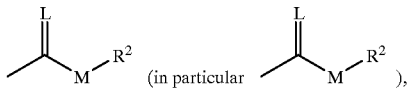  (in particular )

-continued

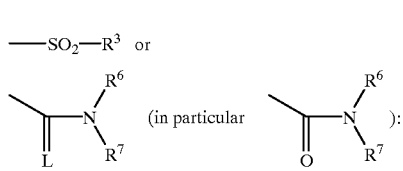
(d)

Moreover, especially preferred compounds of the formula (I) are those in which Het represents the group

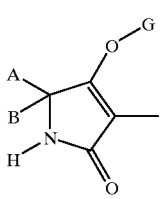
(1)

Moreover, especially preferred compounds of the formula (I) are those in which Het represents the group

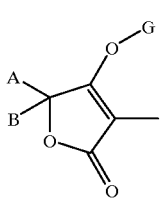
(2)

Moreover, especially preferred compounds of the formula (I) are those in which Het represents the group

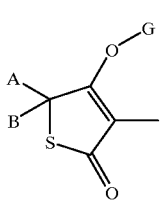
(3)

As far as this is possible, saturated or unsaturated hydrocarbon radicals, such as alkyl or alkenyl, can be in each case straight-chain or branched, also in conjunction with hetero atoms such as, for example, in alkoxy.

Optionally substituted radicals can be monosubstituted or polysubstituted, it being possible for the substituents to be identical or different in the case of polysubstitutions.

In addition to the compounds mentioned in the Preparation Examples, the following compounds of the formula (I-1-a) may be mentioned individually:

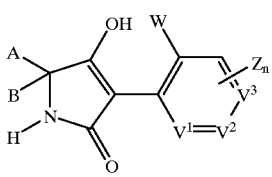

TABLE 1

$W = CH_3; V^1 = CCH_3; V^2 = N; V^3 = CH; Z_n = H$

| A | B |
|---|---|
| $CH_3$ | H |
| $C_2H_5$ | H |
| $C_3H_7$ | H |
| $i\text{-}C_3H_7$ | H |
| $C_4H_9$ | H |
| $i\text{-}C_4H_9$ | H |
| $s\text{-}C_4H_9$ | H |
| $t\text{-}C_4H_9$ | H |
| $CH_3$ | $CH_3$ |
| $C_2H_5$ | $CH_3$ |
| $C_3H_7$ | $CH_3$ |
| $i\text{-}C_3H_7$ | $CH_3$ |
| $C_4H_9$ | $CH_3$ |
| $i\text{-}C_4H_9$ | $CH_3$ |
| $s\text{-}C_4H_9$ | $CH_3$ |
| $t\text{-}C_4H_9$ | $CH_3$ |
| $C_2H_5$ | $C_2H_5$ |
| $C_3H_7$ | $C_3H_7$ |
|  | $CH_3$ |
| 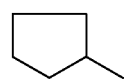 | $CH_3$ |
| 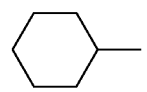 | $CH_3$ |
| $-(CH_2)_2-$ | |
| $-(CH_2)_4-$ | |
| $-(CH_2)_5-$ | |
| $-(CH_2)_6-$ | |
| $-(CH_2)_7-$ | |
| $-(CH_2)_2-O-(CH_2)_2-$ | |
| $-(CH_2)_2-S-(CH_2)_2-$ | |
| $-CH_2-CHCH_3-(CH_2)_3-$ | |
| $-(CH_2)_2-CHCH_3-(CH_2)_2-$ | |
| $-(CH_2)_2-CHC_2H_5-(CH_2)_2-$ | |
| $-(CH_2)_2-CHC_3H_7-(CH_2)_2-$ | |
| $-(CH_2)_2-CHi-C_3H_7-(CH_2)_2-$ | |
| $-(CH_2)_2-CHOCH_3-(CH_2)_2-$ | |
| $-(CH_2)_2-CHOC_2H_5-(CH_2)_2-$ | |
| $-(CH_2)_2-CHOC_3H_7-(CH_2)_2-$ | |
| $-(CH_2)_2-CHOi-C_3H_7-(\#_2)_2-$ | |
| $-(CH_2)_2-C(CH_3)_2-(CH_2)_2-$ | |
| $-CH_2-(CHCH_3)_2-(CH_2)_2-$ | |
| 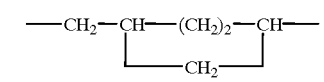 | |
| 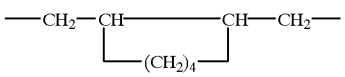 | |
| 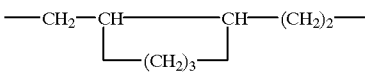 | |
| 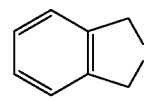 | |

TABLE 1-continued

W = CH$_3$; V$^1$ = CCH$_3$; V$^2$ = N; V$^3$ = CH; Z$_n$ = H

| A | B |
|---|---|
| 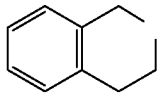 | |

Table 2: A and B have the same meanings as in Table 1 and W=CH$_3$; V$^1$=CCl; V$^2$=N; V$^3$=CH; Z$_n$=H Table 3: A and B have the same meanings as in Table 1 and W=CH$_3$; V$^1$=CCH$_3$; V$^2$=N; V$^3$=CCH$_3$; Z$_n$=H Table 4: A and B have the same meanings as in Table 1 and W=H; V$^1$=CCl; V$^2$=N; V$^3$=CH; Z$_n$=H Table 5: A and B have the same meanings as in Table 1 and W=CH$_3$; V$^1$=N; V$^2$=CH; V$^3$=CCH$_3$; Z$_n$=H Table 6: A and B have the same meanings as in Table 1 and W=Cl; V$^1$=N; V$^2$=CH; V$^3$=CCl; Z$_n$=H Table 7: A and B have the same meanings as in Table 1 and W=Cl; V$^1$=N; V$^2$=CH; V$^3$=CCH$_3$; Z$_n$ H Table 8: A and B have the same meanings as in Table 1 and W=CH$_3$; V$^1$=N; V$^2$=CH; V$^3$=CCl; Z$_n$ H Table 9: A and B have the same meanings as in Table 1 and W=CH$_3$; V$^1$=CH; V$^2$=CH; V$^3$=N; Z$_n$=H Table 10: A and B have the same meanings as in Table 1 and W=H; V$^1$=C—Cl; V$^2$=N; V$^3$=C—Cl; Z$_n$=H Table 11: A and B have the same meanings as in Table 1 and W=Cl; V$^1$=CH; V$^2$=N; V$^3$=C—Cl; Z$_n$=H In addition to the compounds mentioned in the Preparation Examples, the following compounds of the formula (I-2-a) may be mentioned individually:

TABLE 12

W = CH$_3$; V$^1$ = CCH$_3$; V$^2$ = N; V$^3$ = CH; Z$_n$ = H

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| 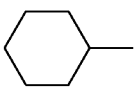 | CH$_3$ |

TABLE 12-continued

W = CH$_3$; V$^1$ = CCH$_3$; V$^2$ = N; V$^3$ = CH; Z$_n$ = H

| A | B |
|---|---|
|  | CH$_3$ |
|  | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi—C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHOi—C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
| —CH$_2$—CH —(CH$_2$)$_2$— | |

Table 13: A and B have the same meanings as in Table 12 and W=CH$_3$; V$^1$=CCl; V$^2$=N; V$^3$=CH; Z$_{n=H}$ Table 14: A and B have the same meanings as in Table 12 and W=CH$_3$; V$^1$=CCH$_3$; V$^2$=N; V$^3$=CCH$_3$; Z$_n$=H Table 15: A and B have the same meanings as in Table 12 and W=H; V$^1$=CCl; V$^2$=N; V$^3$=CH; Z$_n$=H Table 16: A and B have the same meanings as in Table 12 and W=CH$_3$; V$^1$=N; V$^2$=CH; V$^3$=CCH$_3$; Z$_n$=H Table 17: A and B have the same meanings as in Table 12 and W=Cl; $V^1$=N; $V^2$=CH; $V^3$=CCl; $Z_n$=H Table 18: A and B have the same meanings as in Table 12 and W=Cl; $V^1$=N; $V^2$=CH; $V^3$=CCH$_3$; $Z_n$=H Table 19: A and B have the same meanings as in Table 12 and W=CH$_3$; $V^1$=N; $V^2$=CH; $V^3$=CCl; $Z_n$=H Table 20: A and B have the same meanings as in Table 12 and W=CH$_3$; $V^1$=CH; $V^2$=CH; $V^3$=N; $Z_n$=H Table 21: A and B have the same meanings as in Table 12 and W=H; $V^1$=C—Cl; $V^2$=N; $V^3$=C—Cl; $Z_n$=H Table 22: A and B have the same meanings as in Table 12 and W=Cl; $V^1$=CH; $V^2$=N; $V^3$=C—Cl; $Z_n$=H In addition to the compounds mentioned in the Preparation Examples, the following compounds of the formula (I-3-a) may be mentioned individually:

TABLE 23

$W = CH_3; V^1 = CCH_3; V^2 = N; V^3 = CH; Z_n = H$

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| cyclopropyl | CH$_3$ |
| cyclopentyl | CH$_3$ |
| cyclohexyl | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi—C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |

TABLE 23-continued $W = CH_3; V^1 = CCH_3; V^2 = N; V^3 = CH; Z_n = H$

| A | B |
|---|---|
| —(CH$_2$)$_2$—CHOC$_3$H$_7$—(CH$_2$)$_2$— | |
| —(CH$_2$)$_2$—CHOi—C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
| —CH$_2$—CH—(CH$_2$)$_2$—CH— with —CH$_2$— bridge | |
| —CH$_2$—CH—CH—CH$_2$— with —(CH$_2$)$_4$— bridge | |
| —CH$_2$—CH—CH—(CH$_2$)$_2$— with —(CH$_2$)$_3$— bridge | |
| indanyl | |
| tetrahydronaphthyl | |

Table 24: A and B have the same meanings as in Table 23 and W=CH$_3$; $V^1$=CCl; $V^2$=N; $V^3$CH; $Z_n$=H Table 25: A and B have the same meanings as in Table 23 and W=CH$_3$; $V^1$=CCH$_3$; $V^2$=N; $V^3$=CH$_3$; $Z_n$=H Table 26: A and B have the same meanings as in Table 23 and W=Cl; $V^1$=N; $V^2$=CH; $V^3$=CCl; $Z_n$=H Table 27: A and B have the same meanings as in Table 23 and W=CH$_3$; $V^1$=CH; $V^2$=CH; $V^3$=N; $Z_n$=H Table 28: A and B have the same meanings as in Table 23 and W=H; $V^1$=C—Cl; $V^2$N; $V^3$=C—Cl; $Z_n$=H Table 29: A and B have the same meanings as in Table 23 and W=Cl; $V^1$=CH; $V^2$=N; $V^3$=C—Cl; $Z_n$=H In addition to the compounds mentioned in the Preparation Examples, the following compounds of the formula (I-4-a) may be mentioned individually:

TABLE 30

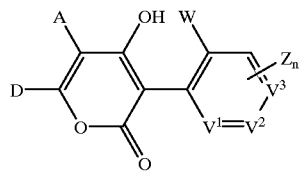

W = CH$_3$; V$^1$ = CCH$_3$; V$^2$ = N; V$^3$ = CH; Z$_n$ = H

| A | D |
|---|---|
| H | CH$_3$ |
| H | C(CH$_3$)$_3$ |
| H | C(CH$_3$)$_2$CH$_2$Cl |
| CH$_3$ | CH$_3$ |
| CH$_3$ | CH$_2$CHCH$_3$CH$_2$CH$_3$ |
| H | CH=C(CH$_3$)$_2$ |
| CH$_3$ | —C$_6$H$_4$-F (4-F) |
| CH$_3$ | —C$_6$H$_4$-Cl (4-Cl) |
| CH$_3$ | —C$_6$H$_3$-F,F (2,4-F) |
| CH$_3$ | —C$_6$H$_3$-Cl,Cl (3,4-Cl) |
| CH$_3$ | —C$_6$H$_4$-OCF$_3$ (4-OCF$_3$) |
| CH$_3$ | —C$_6$H$_5$ |
| H | 2-furyl |
| CH$_3$ | 2-thienyl |
| CH$_3$ | 2-pyridyl |
| CH$_3$ | 3-pyridyl |

TABLE 30-continued

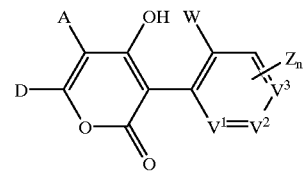

W = CH$_3$; V$^1$ = CCH$_3$; V$^2$ = N; V$^3$ = CH; Z$_n$ = H

| A | D |
|---|---|
| CH$_3$ | 4-pyridyl |
| H | 2,4-dimethyl-5-thiazolyl (with 2-CH$_3$) |
| CH$_3$ | C$_5$H$_9$ |
| CH$_3$ | C$_3$H$_5$ |
| H | C$_3$H$_4$Cl |
| | (CH$_2$)$_3$ |
| | (CH$_2$)$_4$ |
| | C(CH$_3$)$_2$OC(CH$_3$)$_2$ |

Table 31: A and D have the same meanings as in Table 30 and W=CH$_3$; V$^1$=CCl; V$^2$=N; V$^3$=CH; Z$_n$=H Table 32: A and D have the same meanings as in Table 30 and W=CH$_3$; V$^1$=CCH$_3$; V$^2$=N; V$^3$=CCH$_3$; Z$_n$=H Table 33: A and D have the same meanings as in Table 30 and W=Cl; V$^1$=N; V$^2$=CH; V$^3$=CCl; Z$_n$=H Table 34: A and D have the same meanings as in Table 30 and W=CH$_3$; V$^1$=CH; V$^2$=CH; V$^3$=N; Z$_n$=H In addition to the compounds mentioned in the preparation examples, the following compounds of the formula (I-5-a) may be mentioned individually:

TABLE 35

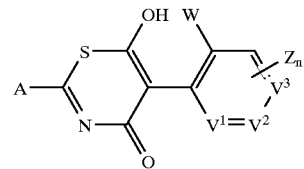

W = CH$_3$; V$^1$ = CCH$_3$; V$^2$ = N; V$^3$ = CH; Z$_n$ = H

| A |
|---|
| CH$_3$ |
| CH(CH$_3$)$_2$ |
| —C$_6$H$_5$ |
| —C$_6$H$_4$-F |

TABLE 35-continued

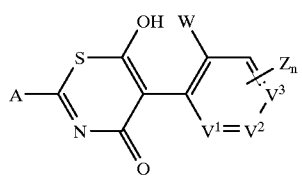

W = CH$_3$; V$^1$ = CCH$_3$; V$^2$ = N; V$^3$ = CH; Z$_n$ = H

A

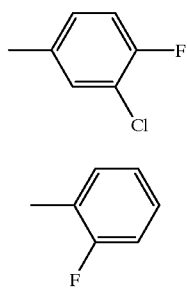

Table 36: A has the same meaning as in Table 35 and W=CH$_3$; V$^1$=CCl; V$^2$=N; V$^3$=CH; Z$_n$=H Table 37: A has the same meaning as in Table 35 and W=CH$_3$; V$^1$=CCH$_3$; V$^2$=N; V$^3$=CCH$_3$; Z$_n$=H Table 38: A has the same meaning as in Table 35 and W=Cl; V$^1$=N; V$^2$=CH; V$^3$=CCl; Z$_n$=H Table 39: A has the same meaning as in Table 35 and W=CH$_3$; V$^1$=CH; V$^2$=CH; V$^3$=N; Z$_n$=H If, in accordance with process (A), ethyl N-[3-(6-chloro-2,4-dimethyl)-pyridylacetyl]-1-amino-4-ethyl-cyclohexane-carboxylate is used as starting substance, the course of the process according to the invention can be represented by the following equation:

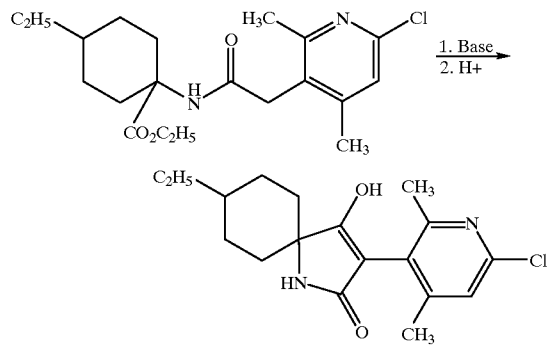

If, in accordance with process (B), ethyl O-[4-(3-chloro-5-methyl)-pyridylacetyl]-hydroxyacetate is used, the course of the process according to the invention can be represented by the following equation:

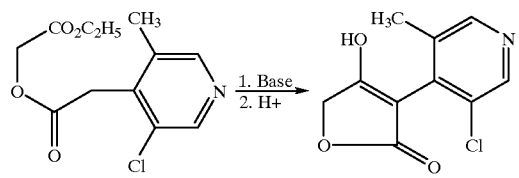

If, in accordance with process (C), ethyl 2-[2-(3-chloro-5-methyl)-pyridyl]-4-(4-methoxy)-benzylmercapto-4-methyl-3-oxo-valerate is used as starting substance, the course of the process according to the invention can be represented by the following equation:

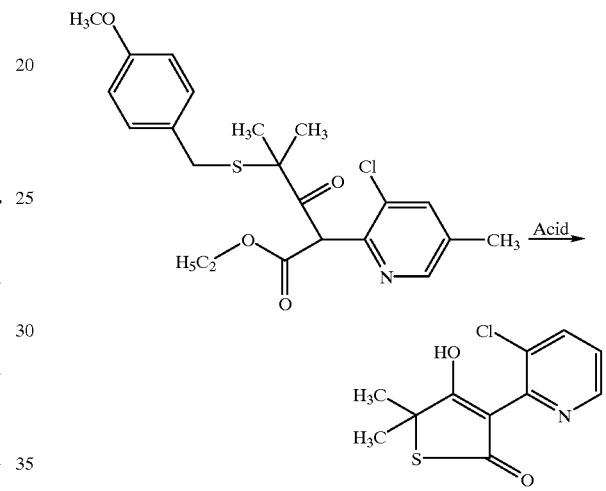

For example, if, in accordance with process (D), chlorocarbonyl 2-[3-(6-chloro-2,4-dimethyl)-pyridyl] ketene and acetone are used as starting compounds, the course of the process according to the invention can be represented by the following equation:

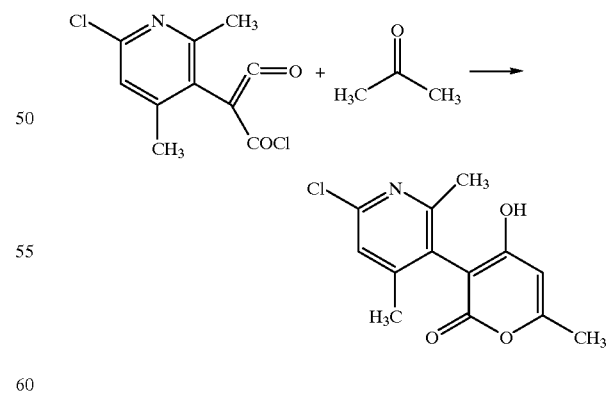

For example, if, in accordance with process (E), chlorocarbonyl 2-[3-(2,4,6-trimethyl)-pyridyl] ketene and thiobenzamide are used as starting compounds, the course of the process according to the invention can be represented by the following equation:

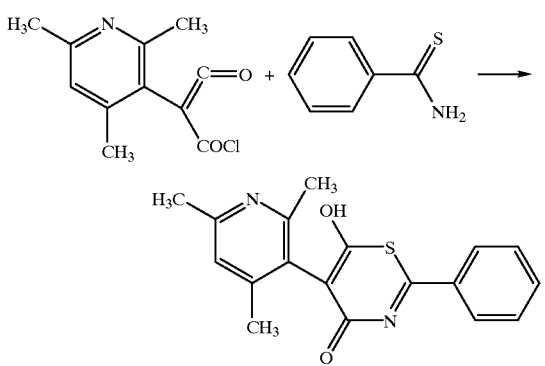

If, in accordance with process (Fα), 3-[4-(3-chloro-5-methyl)-pyridyl]-5,5-dimethyl-pyrrolidine-2,4-dione and pivaloyl chloride are used as starting materials, the course of the process according to the invention can be represented by the following equation:

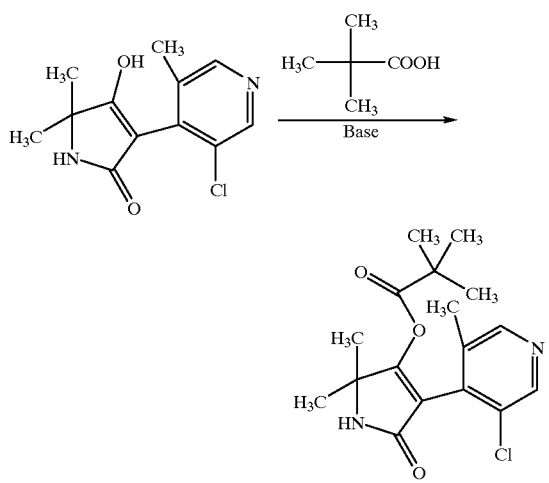

If, in accordance with process (F) (variant β), 3-[2-(3-chloro)-pyridyl]-4-hydroxy-5-phenyl-Δ³-dihydrofuran-2-one and acetic anhydride are used as starting compounds, the course of the process according to the invention can be represented by the following equation:

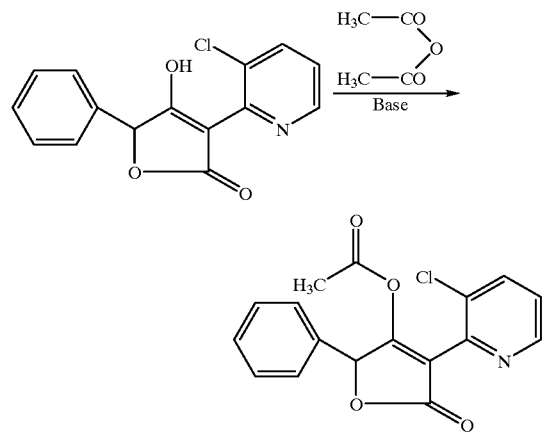

If, in accordance with process (G), 8-[2-(3,5-dichloro-4-methyl)-pyridyl]-5,5-pentamethylene-pyrrolidine-2,4-dione and ethoxyethyl chloroformate are used as starting compounds, the course of the process according to the invention can be represented by the following equation:

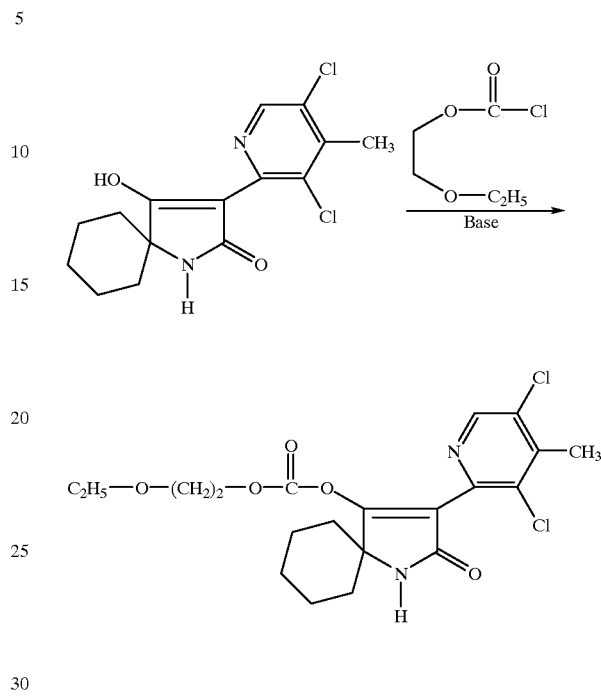

If, in accordance with process (H) (variant α), 3-[2-(3-bromo-5,6-dimethyl)-pyridyl]-4-hydroxy-6-(3-pyridyl)-pyrone and methyl chloromonothioformate are used as starting materials, the course of the process according to the invention can be represented as follows:

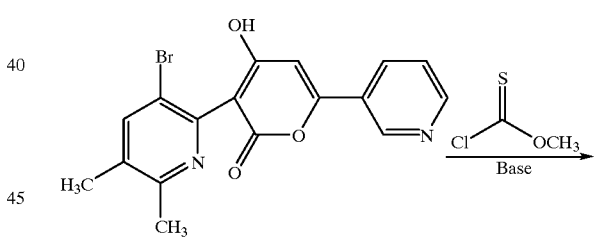

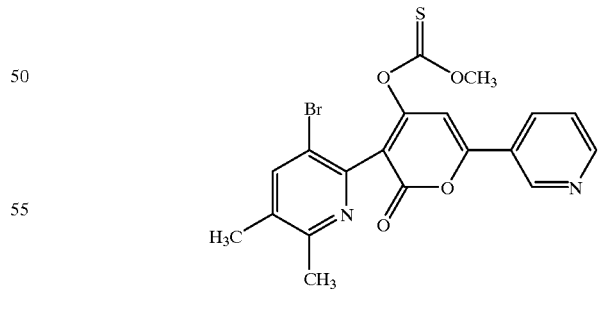

If, in accordance with process (H) (variant β), 5-[4-(2-chloro-3,5-dimethyl)-pyridyl]-6-hydroxy-2-(4-chlorophenyl)-thiazin-4-one, carbon disulphide and methyl iodide are used as starting components, the course of the reaction can be represented as follows:

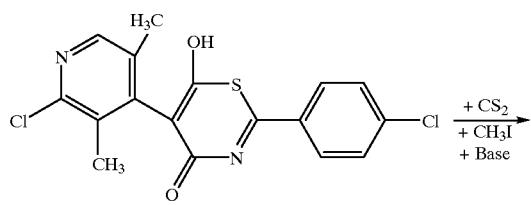

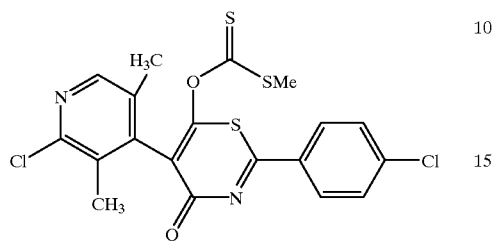

If, in accordance with process (I), 2-[3-(2,4,6-trimethyl)-pyridyl]-5,5[-3-methyl)pentamethylene-pyrrolidine-2,4-dione and methanesulphonyl chloride are used as starting materials, the course of the reaction can be represented by the following equation:

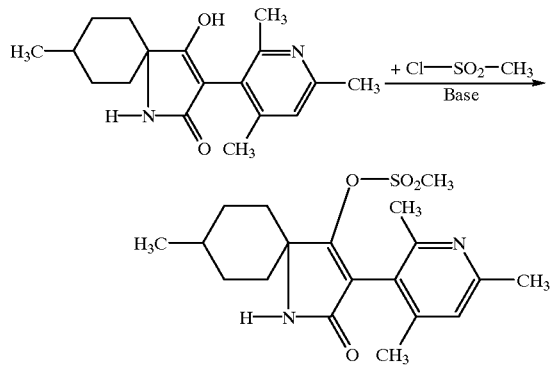

If, in accordance with process (J), 2-[4-(3-chloro-5-methyl)-pyridyl]-4-hydroxy-5-methyl-6-(2-pyridyl)-pyrone and 2,2,2-trifluoroethyl methanechlorothiophosphonate are used as starting materials, the course of the reaction can be represented by the following equation:

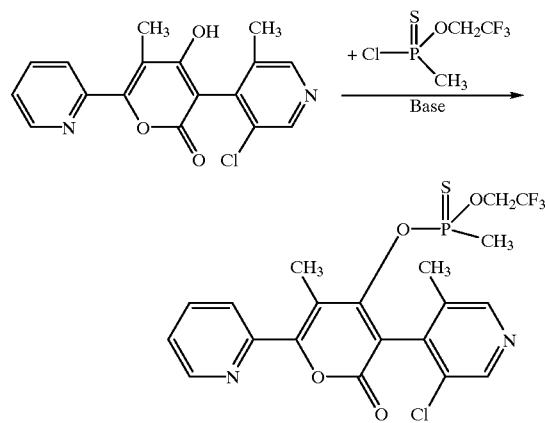

If, in accordance with process (K), 3-[3-(2,6-dichloro)-4-methylpyridyl]-5-cyclopropyl-5-methyl-pyrrolidine-2,4-dione and NaOH are used as components, the course of the process according to the invention can be represented by the following equation:

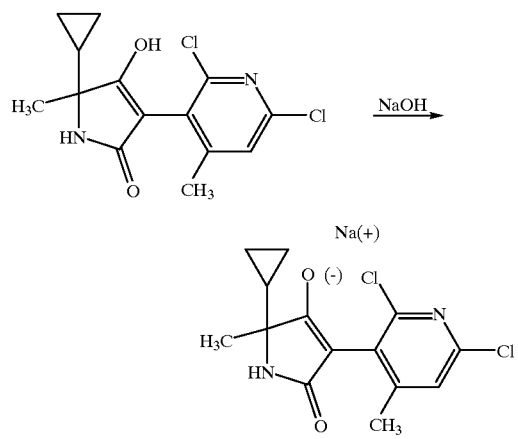

If, in accordance with process (L) (variant α), 3-[3-(2-chloro-6-bromo-5-methyl)-pyridyl]-4-hydroxy-5,5-tetramethylene-Δ³-dihydro-furan-2-one and ethyl isocyanate are used as starting materials, the course of the reaction can be represented by the following equation:

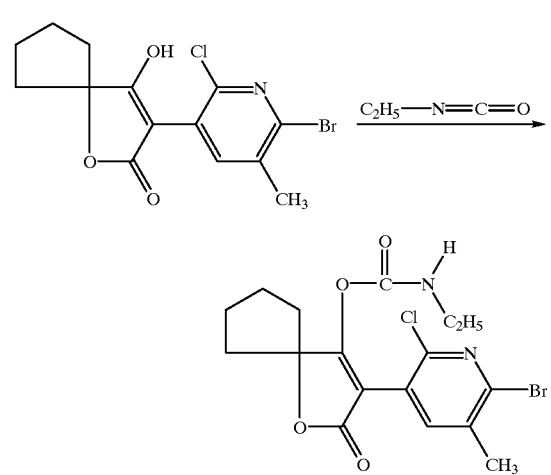

If, in accordance with process (L) (variant β), 3-[4-(3-chloro-5-methyl)-pyridyl]-5-methyl-pyrrolidine-2,4-dione and dimethylcarbamoyl chloride are used as starting materials, the course of the reaction can be represented by the following equation:

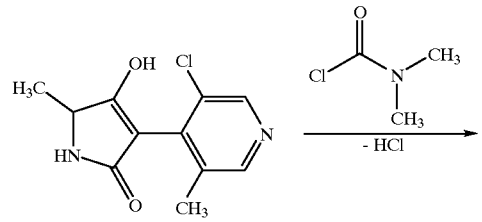

-continued

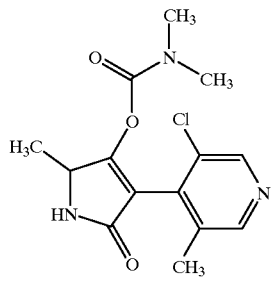

The compounds of the formula (II)

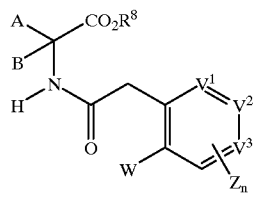
(II)

in which

A, B, W, X, Z, $V^1$, $V^2$, $V^3$, n and $R^8$ have the abovementioned meanings and which are required as starting materials in process (A) according to the invention are new.

For example, the acylamino acid esters of the formula (II) are obtained when amino acid derivatives of the formula (XIX)

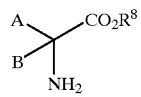
(XIX)

in which

A, B and $R^8$ have the abovementioned meanings are acylated with substituted pyridylacetic acid halides of the formula (XX)

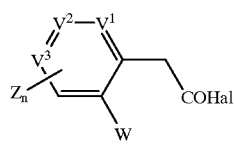
(XX)

in which

W, $V^1$, $V^2$, $V^3$, n and Z have the abovementioned meanings and Hal represents chlorine or bromine, (Chem. Reviews 52, 237–416 (1953); Bhattacharya, Indian J. Chem. 6 341–5, 1968), or when acylamino acids of the formula (XXI)

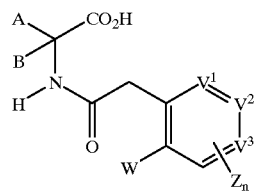
(XXI)

in which

A, B, W, $V^1$, $V^2$, $V^3$, n and Z have the abovementioned meanings are esterified (Chem. Ind. (London) 1568 (1968)).

The compounds of the formula (XXI)

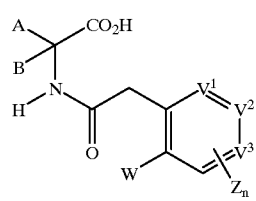
(XXI)

in which

A, B, W, $V^1$, $V^2$, $V^3$, n and Z have the abovementioned meanings are new.

The compounds of the formula (XXI) are obtained when amino acids of the formula (XXII)

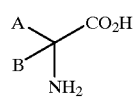
(XXII)

in which

A and B have the abovementioned meanings are acylated with substituted pyridylacetic acid halides of the formula (XX)

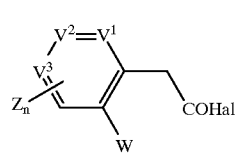
(XX)

in which

W, $V^1$, $V^2$, $V^3$, n and Z have the abovementioned meanings and Hal represents chlorine or bromine by the method of Schotten-Baumann (Organikum, VEB Deutscher Verlag der Wissenschaften, Berlin 1977, p. 505).

Some of the compounds of the formula (XX) are new. They can be prepared by known processes.

For example, the compounds of the formula (XX) are obtained by reacting substituted pyridylacetic acids of the formula (XXIII)

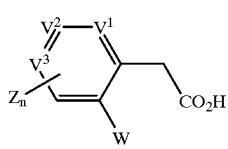

(XXIII)

in which

W, $V^1$, $V^2$, $V^3$, n and Z have the abovementioned meanings with halogenating agents (for example thionyl chloride, thionyl bromide, oxalyl chloride, phosgene, phosphorus trichloride, phosphorus tribromide or phosphorus pentachloride) at temperatures from −20° C. to 150° C., preferably from −10° C. to 100° C., if appropriate in the presence of a diluent (for example optionally chlorinated aliphatic or aromatic hydrocarbons such as toluene or methylene chloride).

Some of the compounds of the formula (XXIII) are new. They can be prepared by processes known from the literature (see, for example, Organikum, 15th Edition, p. 533, VEB Deutscher Verlag der Wissenschaften, Berlin 1977 and the Preparation Examples). The compounds of the formula (XXIII) are obtained, for example, by hydrolysing substituted pyridylacetic acid esters of the formula (XXIV)

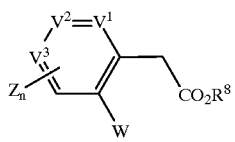

(XXIV)

in which

W, $V^1$, $V^2$, $V^3$, n, Z and $R^8$ have the abovementioned meanings at temperatures between 0° C. and 150° C., preferably between 20° C. and 100° C., in the presence of an acid (for example an inorganic acid such as hydrochloric acid) or of a base (for example an alkali metal hydroxide such as sodium hydroxide or potassium hydroxide) and, if appropriate, of a diluent (for example an aqueous alcohol such as methanol or ethanol).

Some of the compounds of the formula (XXIV) are new. They can be prepared by processes known in principle.

For example, the compounds of the formula (XXIV) are obtained by reacting substituted 1,1,1-trichloro-2-pyridylethanes of the formula (XXV)

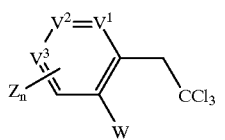

(XXV)

in which

W, $V^1$, $V^2$, $V^3$, n and Z have the abovementioned meanings first with alkoxides (for example alkali metal alkoxides such as sodium methoxide or sodium ethoxide) in the presence of a diluent (for example the alcohol derived from the alkoxide) at temperatures between 0° C. and 150° C., preferably between 20° C. and 120° C., and subsequently with an acid (preferably an inorganic acid such as, for example, sulphuric acid) at temperatures between −20° C. and 150° C., preferably 0° C. and 100° C. (cf DE 3 314 249).

The compounds of the formula (XXV) are new. They can be prepared by processes known in principle.

For example, the compounds of the formula (XXV) are obtained when aminopyridines of the formula (XXVI)

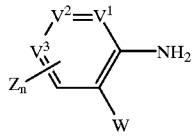

(XXVI)

in which

W, $V^1$, $V^2$, $V^3$, n and Z have the abovementioned meanings are reacted with vinylidene chloride ($CH_2=CCl_2$) in the presence of an alkyl nitrite of the formula (XXVII)

$R^{21}$—ONO  (XXVII)

in which $R^{21}$ represents alkyl, preferably $C_1$–$C_6$-alkyl, in the presence of copper(II) chloride and, if appropriate, in the presence of a diluent (for example an aliphatic nitrile such as acetonitrile) at a temperature of −20° C. to 80° C., preferably 0° C. to 60° C.

The compounds of the formulae (XXVI) and (XXVII) are known compounds of organic chemistry. Copper(II) chloride and vinylidene chloride have been known for a long time and are commercially available.

The compounds of the formulae (XIX) and (XXII) are known in some cases and/or can be synthesized by known processes (see, for example, Compagnon, Ann. Chim. (Paris) [14] 5, pp. 11–22, 23–27 (1970)).

The substituted cyclic aminocarboxylic acids of the formula (XXIIa) in which A and B form a ring are generally obtainable by a Bucherer-Bergs synthesis or by a Strecker synthesis, where they are obtained in each case in different isomeric forms. Thus, the conditions of the Bucherer-Bergs synthesis preferentially yields the isomers (termed 13 hereinbelow for the sake of simplicity) in which the radicals R and the carboxyl group are in the equatorial position, while the conditions of the Strecker synthesis preferentially yield the isomers (termed α hereinbelow for the sake of simplicity) in which the amino group and the radicals R are in the equatorial position

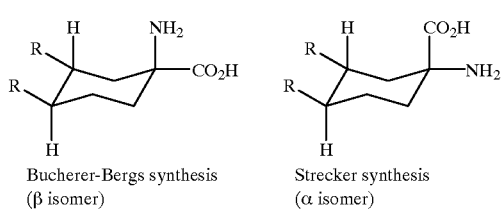

Bucherer-Bergs synthesis (β isomer)   Strecker synthesis (α isomer)

(L. Munday, J. Chem. Soc. 4372 (1961); J. T. Eward, C. Jitrangeri, Can. J. Chem. 53, 3339 (1975)).

Moreover, the starting materials of the formula (II)

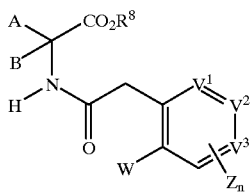
(II)

in which

A, B, W, $V^1$, $V^2$, $V^3$, n, Z and $R^8$ have the abovementioned meanings and which are used in the above process (A) can be prepared when aminonitriles of the formula (XXVIII)

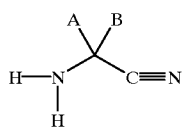
(XXVIII)

in which

A and B have the abovementioned meanings are reacted with substituted pyridylacetic acid halides of the formula (XX)

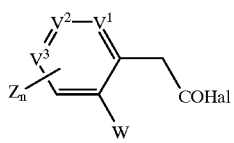
(XX)

in which

W, $V^1$, $V^2$, $V^3$, n, Z and Hal have the abovementioned meanings to give compounds of the formula (XXIX)

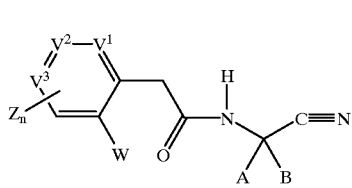
(XXIX)

in which

A, B, W, $V^1$, $V^2$, $V^3$, n and Z have the abovementioned meanings and these are subsequently subjected to acid alcoholysis.

The compounds of the formula (XXIX) are also new.
The compounds of the formula (III)

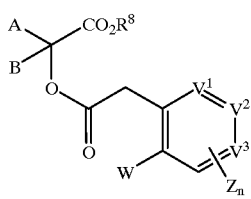
(III)

in which

A, B, W, $V^1$, $V^2$, $V^3$, n, Z and $R^8$ have the abovementioned meanings and which are required as starting materials in process (B) according to the invention are new.

They can be prepared in a simple manner by methods known in principle.

The compounds of the formula (III) are obtained, for example when 2-hydroxycarboxylic esters of the formula (XXX)

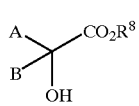
(XXX)

in which

A, B and $R^8$ have the abovementioned meanings are acylated with substituted pyridylacetyl halides of the formula (XX)

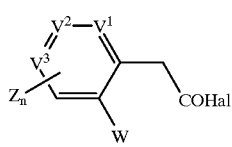
(XX)

in which

W, $V^1$, $V^2$, $V^3$, n, Z and Hal have the abovementioned meanings (Chem. Reviews 52, 237–416 (1953)).

Moreover, compounds of the formula (III) are obtained when substituted pyridylacetic acids of the formula (XXIII)

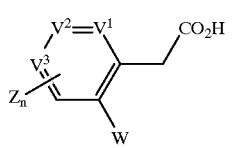
(XXIII)

in which

W, $V^1$, $V^2$, $V^3$, n and Z have the abovementioned meanings are alkylated with a-halogenocarboxylic esters of the formula (XXXI)

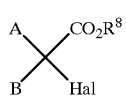
(XXXI)

in which

A, B and $R^8$ have the abovementioned meanings and Hal represents chlorine or bromine.

The compounds of the formula (XXXI) are commercially available or can be prepared in a simple manner by known methods.

The compounds of the formula (IV)

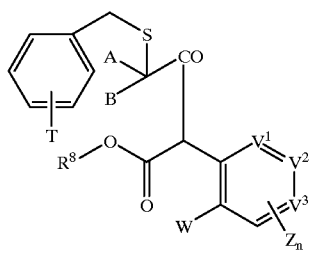

(IV)

in which

A, B, T, W, $V^1$, $V^2$, $V^3$, n, Z and $R^8$ have the abovementioned meanings and which are required as starting materials in the above process (C) are new.

They can be prepared by methods known in principle.

The compounds of the formula (IV) are obtained, for example, when substituted pyridylacetic esters of the formula (XXIV)

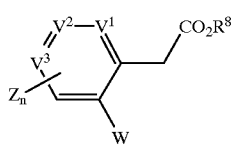

(XXIV)

in which

W, $V^1$, $V^2$, $V^3$, n, $R^8$ and Z have the abovementioned meanings are acylated with 2-benzylthio-carboxylic acid halides of the formula (XXXII)

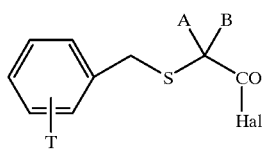

(XXXII)

in which

A, B and T have the abovementioned meanings and Hal represents halogen (in particular chlorine or bromine) in the presence of strong bases (see, for example, M. S. Chambers, E. J. Thomas, D. J. Williams, J. Chem. Soc. Chem. Commun., (1987), 1228).

The benzylthio-carboxylic acid halides of the formula (XXXII) are known in some cases and/or can be prepared by known methods (J. Antibiotics (1983), 26, 1589).

The halogenocarbonyl ketenes of the formula (VI) which are required as starting materials in process (D) are new. They can be prepared in a simple manner by methods known in principle (cf., for example, Org. Prep. Proced. Int. 7, (4), 155–158, 1975 and DE 1 945 703). The compounds of the formula (VI)

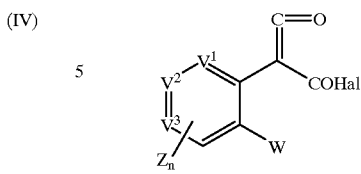

(VI)

in which

W, $V^1$, $V^2$, $V^3$, n and Z have the abovementioned meanings and Hal represents chlorine or bromine are obtained when substituted pyridylmalonic acids of the formula (XXXIII)

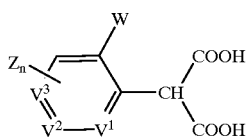

(XXXIII)

in which

W, $V^1$, $V^2$, $V^3$, n and Z have the abovementioned meanings are reacted with acid halides such as, for example, thionyl chloride, phosphorus(V) chloride, phosphorus(III) chloride, oxalyl chloride, phosgene or thionyl bromide, if appropriate in the presence of catalysts such as, for example, diethylformamide, methyl-sterylformamide or triphenylphosphine and, if appropriate, in the presence of bases such as, for example, pyridine or triethylamine at a temperature between –20° C. and 200° C., preferably between 0° C. and 150° C.

The substituted pyridylmalonic acids of the formula (XXXIII) are new. However, they can be prepared in a simple manner by known processes (cf., for example, Organikum, VEB Deutscher Verlag der Wissenschaften, Berlin 1977, p. 517 et seq.), for example by hydrolysing substituted pyridylmalonic esters of the formula (XXXIV)

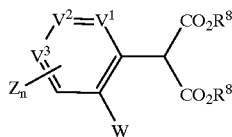

(XXXIV)

in which

W, $V^1$, $V^2$, $V^3$, n, Z and $R^8$ have the abovementioned meanings.

The carbonyl compounds of the formula (V) or their silyl enol ethers of the formula (Va)

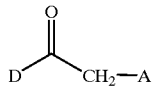

(V)

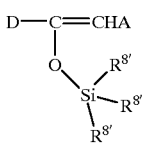

(Va)

in which

A, D and $R^8$ have the abovementioned meanings and which are required as starting materials for process (E) according to the invention are compounds which are commercially available, generally known or accessible by known methods.

The preparation of the ketene acid chlorides of the formula (VI) which are required as starting materials for carrying out process (E) according to the invention has already been described in process (D) according to the invention. The thioamides of the formula (VII)

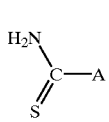

(VII)

in which

A has the abovementioned meaning and which are required for carrying out process (E) according to the invention are compounds generally known in organic chemistry.

The malonic esters of the formula (XXXIV)

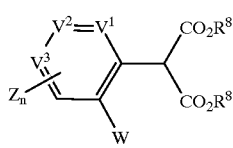

(XXXIV)

in which $R^8$, W, $V^1$, $V^2$, $V^3$, n and Z have the abovementioned meanings are new. They can be synthesized by generally known methods of organic chemistry (cf., for example, Tetrahedron Lett. 27, 2763 (1986) and Organikum, VEB Deutscher Verlag der Wissenschaften, Berlin 1977, p. 587 et seq.).

The acid halides of the formula (VIII), carboxylic anhydrides of the formula (IX), chloroformic esters or chloroformic thioesters of the formula (X), chloromonothioformic esters or chlorodithioformic esters of the formula (XI), alkyl halides of the formula (XII), sulphonyl chlorides of the formula (XIII), phosphorus compounds of the formula (XIV) and metal hydroxides, metal alkoxides or amines of the formula (XV) and (XVI) and isocyanates of the formula (XVII) and carbamoyl chlorides of the formula (XVIII), all of which are furthermore required as starting materials for carrying out processes (F), (G), (H), (I), (J), (K) and (L) according to the invention, are generally known compounds of organic or inorganic chemistry.

In addition, the compounds of the formulae (V), (Va), (VII) to (XIX), (XXII), (XXVIII), (XXX), (XXXI) and (XXXII) are disclosed in the patent applications cited at the outset and/or can be prepared by the methods given therein.

Process (A) is characterized in that compounds of the formula (II) in which A, B, W, $V^1$, $V^2$, $V^3$, n, Z and $R^8$ have the abovementioned meanings are subjected to an intramolecular condensation reaction in the presence of a diluent and in the presence of a base.

Diluents which may be employed in process (A) according to the invention are all organic solvents which are inert to the reactants. The following may preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methyl-pyrrolidone, and alcohols such as methanol, ethanol, propanol, iso-propanol, butanol, iso-butanol and tert-butanol.

Bases (deprotonating agents) which can be employed when carrying out process (A) according to the invention are all customary proton acceptors. The following may preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethyoxyethyl)-amine). Moreover, alkali metals such as sodium or potassium can be used. Substances which may also be employed are alkali metal amides, alkali metal hydrides, alkaline earth metal amides and alkaline earth metal hydrides such as sodium amide, sodium hydride and calcium hydride, and furthermore also alkali metal alkoxides, such as sodium methoxide, sodium ethoxide and potassium tert-butoxide.

When carrying out process (A) according to the invention, the reaction temperature can be varied within a substantial range. In general, the process is carried out at temperatures between –70° C. and 150° C., preferably between –50° C. and 100° C.

Process (A) according to the invention is generally carried out under atmospheric, pressure.

When carrying out process (A) according to the invention, the reactant of the formula (II) and the deprotonating base are generally employed in equimolar to approximately twice the equimolar amounts. However, it is also possible to use one or the other component in a larger excess (up to 3 mol).

Process (B) is characterized in that compounds of the formula (III) in which A, B, W, $V^1$, $V^2$, $V^3$, n, Z and $R^8$ have the abovementioned meanings are subjected to an intramolecular condensation reaction in the presence of a diluent and in the presence of a base.

Diluents which may be employed in process (B) according to the invention are all organic solvents which are inert to the reactants. The following may preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide and N-methyl-pyrrolidone. Moreover, alcohols such as methanol, ethanol, propanol, iso-propanol, butanol, iso-butanol and tert-butanol can be employed.

Bases (deprotonating agents) which can be employed when carrying out process (B) according to the invention are all customary proton acceptors. The following may preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (=methyltrialkyl ($C_8$–$C_{10}$)ammonium chloride) or TDA 1 (=tris-(methoxyethyoxyethyl)-amine). Moreover, alkali metals such as sodium or potassium can be used. Substances which may also be employed are alkali metal amides, alkali metal hydrides, alkaline earth metal amides and alkaline earth metal hydrides such as sodium amide, sodium hydride and calcium hydride, and furthermore also alkali metal alkoxides, such as sodium methoxide, sodium ethoxide and potassium tert-butoxide.

When carrying out process (B) according to the invention, the reaction temperature can be varied within a substantial range. In general, the process is carried out at temperatures between –75° C. and 150° C., preferably between –50° C. and 100° C.

Process (B) according to the invention is generally carried out under atmospheric pressure.

When carrying out process (B) according to the invention, the reactants of the formula (III) and the deprotonating bases are generally employed in approximately equimolar amounts. However, it is also possible to use one or the other component in a larger excess (up to 3 mol).

Process (C) is characterized in that compounds of the formula (IV) in which A, B, T, W, $V^1$, $V^2$, $V^3$, n, Z and $R^8$ have the abovementioned meanings are subjected to an intramolecular cyclization reaction in the presence of an acid and, if appropriate, in the presence of a diluent.

Diluents which can be employed in process (C) according to the invention are all organic solvents which are inert to the reactants. The following may preferably be used: hydrocarbons such as toluene and xylene, furthermore halogenated hydrocarbons such as dichloromethane, chloroform, ethylene chloride, chlorobenzene, dichlorobenzene, furthermore polar solvents such as dimethyl sulphoxide, sulpholane, dimethylformamide and N-methyl-pyrrolidone. Moreover, alcohols such as methanol, ethanol, propanol, iso-propanol, butanol, iso-butanol and tert-butanol can be employed.

If appropriate, the acid employed may also act as the diluent.

Acids which can be employed in process (C) according to the invention are all customary inorganic and organic acids such as, for example, hydrohalic acids, sulphuric acid, alkyl-, aryl- and haloalkylsulphonic acids; in particular, halogenated alkylcarboxylic acids such as, for example, trifluoroacetic acid, are used.

When carrying out process (C) according to the invention, the reaction temperature can be varied within a substantial range. In general, the process is carried out at temperatures between 0° C. and 250° C., preferably between 50° C. and 150° C.

Process (C) according to the invention is generally carried out under atmospheric pressure.

When carrying out process (C) according to the invention, the reactants of the formula (IV) and the acid are employed, for example, in equimolar amounts. However, if appropriate, it is also possible to employ the acid in catalytic amounts.

Process (D) according to the invention is characterized in that carbonyl compounds of the formula (V) or silyl enol ethers thereof of the formula (Va), in which formulae A and B have the abovementioned meanings, are reacted with ketene acid halides of the formula (VI) in which W, $V^1$, $V^2$, $V^3$, n and Z have the abovementioned meanings, if appropriate in the presence of a diluent and if appropriate in the presence of an acid acceptor.

Diluents which can be employed in process (D) according to the invention are all organic solvents which are inert to the reactants. The following( may preferably be used: hydrocarbons such as o-dichlorobenzene, tetralin, toluene and xylene, furthermore ethers such as dibutyl ether, glycol dimethyl ether and diglycol dimethyl ether, and furthermore polar solvents such as dimethyl sulphoxide, sulpholane, dimethylformamide or N-methyl-pyrrolidone.

Acid acceptors which can be used when carrying out process (D) according to the invention are all customary acid acceptors.

The following may preferably be used: tertiary amines such as triethylamine, pyridine, diazabicyclooctane (DABCO), diazabicycloundecene (DBU), diazabicyclononene (DBN), Hünig base or N,N-dimethyl-aniline.

When carrying out process (D) according to the invention, the reaction temperature can be varied within a substantial range. Expediently, the process is carried out at temperatures between 0° C. and 250° C., preferably between 50° C. and 220° C.

Process (D) according to the invention is preferably carried out under atmospheric pressure.

When carrying out process (D) according to the invention, the reactants of the formulae (V) and (VI) and, if appropriate, the acid acceptor are generally employed in approximately equimolar amounts. However, it is also possible to use one or the other component in a larger excess (up to 5 mol).

Process (E) according to the invention is characterized in that thioamides of the formula (VII) in which A has the abovementioned meaning, are reacted with ketene acid halides of the formula (VI) in which W, $V^1$, $V^2$, $V^3$, n and Z have the abovementioned meanings, if appropriate in the presence of a diluent and if appropriate in the presence of an acid acceptor.

Diluents which can be employed in process variant (E) according to the invention are all inert organic solvents. The following may preferably be used: hydrocarbons such as o-dichlorobenzene, tetralin, toluene and xylene, furthermore ethers such as dibutyl ether, glycol dimethyl ether and diglycol dimethyl ether, and furthermore polar solvents such as dimethyl sulphoxide, sulpholane, dimethylformamide or N-methyl-pyrrolidone.

Acid acceptors which can be used when carrying out process (E) according to the invention are all customary acid acceptors.

The following may preferably be used: tertiary amines such as triethylamine, pyridine, diazabicyclooctane (DABCO), diazabicycloundecene (DBU), diazabicyclononene (DBN), Hünig base or N,N-dimethyl-aniline.

When carrying out process (E) according to the invention, the reaction temperature can be varied within a substantial range. Expediently, the process is carried out at temperatures between 0° C. and 250° C., preferably between 20° C. and 220° C.

Process (E) according to the invention is preferably carried out under atmospheric pressure.

When carrying out process (E) according to the invention, the reactants of the formulae (VII) and (VI) and, if appropriate, the acid acceptors are generally employed in approximately equimolar amounts. However, it is also possible to use one or the other component in a larger excess (up to 5 mol).

Process (Fα) is characterized in that compounds of the formulae (I-1-a) to (I-5-a) are in each case reacted with carboxylic acid halides of the formula (VIII), if appropriate in the presence of a diluent and if appropriate in the presence of an acid-binding agent.

Diluents which can be employed in process (Fα) according to the invention are all solvents which are inert to the acid halides. The following may preferably be used: hydrocarbons such as benzine, benzene, toluene, xylene and tetralin, furthermore halogenohydrocarbons such as methylene chloride, chloroform, carbon tetra-chloride, chlorobenzene and o-dichlorobenzene, moreover ketones, such as acetone and methyl isopropyl ketone, furthermore ethers such as diethyl ether, tetrahydrofuran and dioxane, in addition carboxylic esters, such as ethyl acetate, and also strongly polar solvents such as dimethylformamide, dimethyl sulphoxide and sulpholane. If the acid halide is sufficiently stable to hydrolysis, the reaction can also be carried out in the presence of water.

Acid binders which are suitable when carrying out the reaction in accordance with process (Fα) according to the invention are all customary acid acceptors. The following may preferably be used: tertiary amines such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate, and also alkali metal hydroxides such as sodium hydroxide and potassium hydroxide.

When carrying out process (Fα) according to the invention, the reaction temperature can be varied within a substantial range. In general, the process is carried out at temperatures between −20° C. and +150° C., preferably between 0° C. and 100° C.

When carrying out process (Fα) according to the invention, the starting materials of the formulae (I-1-a) to (I-5-a) and the carboxylic acid halide of the formula (VIII) are generally in each case used in approximately equivalent amounts. However, it is also possible to employ the carboxylic acid halide in a larger excess (up to 5 mol). Working-up is carried out by customary methods.

Process (Fβ) is characterized in that compounds of the formulae (I-1-a) to (I-5-a) are in each case reacted with carboxylic anhydrides of the formula (IX), if appropriate in the presence of a diluent and if appropriate in the presence of an acid-binding agent.

Diluents which can be employed in process (Fβ) according to the invention are preferably those diluents which are also suitable when acid halides are used. Besides, a carboxylic anhydride employed in an excess can also simultaneously act as the diluent.

Acid binders which are optionally added in process (Fβ) are preferably those acid binders which are also suitable when acid halides are used.

When carrying out process (Fβ) according to the invention, the reaction temperature can be varied within a substantial range. In general, the process is carried out at temperatures between −20° C. and +150° C., preferably between 0° C. and 100° C.

When carrying out process (Fβ) according to the invention, the starting materials of the formulae (I-1-a) to (I-5-a) and the carboxylic anhydride of the formula (IX) are generally in each case used in approximately equivalent amounts. However, it is also possible to employ the carboxylic anhydride in a larger excess (up to 5 mol). Working-up is carried out by customary methods.

In general, a procedure is followed in which diluent and excess carboxylic anhydride and also the carboxylic acid being formed are removed by distillation by washing with an organic solvent or with water.

Process (G) is characterized in that compounds of the formulae (I-1-a) to (I-5-a) are reacted in each case with chloroformic esters or chloroformic thioesters of the formula (X), if appropriate in the presence of a diluent and if appropriate in the presence of an acid-binding agent.

Acid binders which are suitable for process (G) according to the invention are all customary acid acceptors. The following may preferably be used: tertiary amines such as triethylamine, pyridine, DABCO, DBU, DBA, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate, and also alkali metal hydroxides such as sodium hydroxide and potassium hydroxide.

Diluents which can be employed in process (G) according to the invention are all solvents which are inert to the chloroformic esters or chloroformic thioesters. The following may preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones, such as acetone and methyl isopropyl ketone, furthermore ethers such as diethyl ether, tetrahydrofuran and dioxane, in addition carboxylic esters, such as ethyl acetate, moreover nitriles such as acetonitrile, and also strongly polar solvents such as dimethylformamide, dimethyl sulphoxide and sulpholane.

When carrying out process (G) according to the invention, the reaction temperature can be varied within a substantial range. In general, the reaction temperature is between −20° C. and +100° C., preferably between 0° C. and 50° C.

Process (G) according to the invention is generally carried out under atmospheric pressure.

When carrying out process (G) according to the invention, the starting materials of the formulae (I-1-a) to (I-5-a) and the relevant chloroformic ester or chloroformic thioester of the formula (X) are generally used in each case in approximately equivalent amounts. However, it is also possible to employ one or the other component in a larger excess (up to 2 mol). Working-up is carried out by customary methods. In general, a procedure is followed in which precipitated salts are removed and the reaction mixture which remains is concentrated by stripping off the diluent.

Process (H) according to the invention is characterized in that compounds of the formulae (I-1-a) to (I-5-a) are reacted in each case with (Hα) compounds of the formula (XI) in the presence of a diluent and, if appropriate, in the presence of an acid binder, or (Hβ) carbon disulphide and subsequently with alkyl halides of the formula (XII), if appropriate in the presence of a diluent and if appropriate in the presence of a base.

In preparation process (Hα), approximately 1 mol of chloromonothioformic ester or chlorodithioformic ester of the formula (XI) is reacted per mole of starting compound of the formulae (I-1-a) to (I-5-a) at 0 to 120° C., preferably at 20 to 60° C.

Suitable diluents which are optionally added are all inert polar organic solvents such as ethers, amides, sulphones, sulphoxides, but also halogenoalkanes.

Dimethyl sulphoxide, tetrahydrofuran, dimethylformamide or methylene chloride are preferably employed.

If, in a preferred embodiment, the enolate salt of the compounds (I-1-a) to (I-5-a) is synthesized by adding strong deprotonating agents such as, for example, sodium hydride or potassium tertiary-butoxide, a further addition of acid binders can be dispensed with.

If acid binders are employed, then suitable substances are customary inorganic or organic bases, with sodium hydroxide, sodium carbonate, potassium carbonate, pyridine and triethylamine being mentioned by way of example.

The reaction can be carried out under atmospheric pressure or under elevated pressure, it is preferably carried out under atmospheric pressure. Working-up is carried out by customary methods.

In preparation process (Hβ), the equimolar amount, or an excess, of carbon disulphide is added in each case per mole of starting compounds of the formulae (I-1-a) to (I-5-a). This process is preferably carried out at temperatures from 0 to 50° C. and, in particular, at 20 to 30° C.

Frequently, it is expedient first to prepare the corresponding salt from the compounds of the formulae (I-1-a) to (I-5-a) by adding a base (such as, for example, potassium tertiary butoxide or sodium hydride). The compounds (I-1-a) to (I-5-a) are reacted with carbon disulphide in each case until the formation of the intermediate is complete, for example after stirring for several hours at room temperature.

Bases which can be employed in process (Hβ) are all customary proton acceptors. The following are preferably usable: alkali metal hydrides, alkali metal alkoxides, alkali metal carbonates, alkali metal hydrogen carbonates, alkaline earth metal carbonates, alkaline earth metal hydrogen carbonates, or nitrogen bases. Examples which may be mentioned are sodium hydride, sodium methoxide, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all customary solvents.

The following may preferably be used: aromatic hydrocarbons such as benzene or toluene, alcohols such as methanol, ethanol, isopropanol or ethylene glycol, nitriles such as acetonitrile, ethers such as tetrahydrofuran or dioxane, amides such as di-methylformamide, or other polar solvents such as dimethyl sulphoxide or sulpholane.

The further reaction with the alkyl halide of the formula (XII) is preferably carried out at 0 to 70° C., in particular at 20 to 50° C. At least the equimolar amount of alkyl halide is employed.

The process is carried out under atmospheric pressure or under elevated pressure, preferably under atmospheric pressure.

Again, working-up is carried out by customary methods.

Process (I) according to the invention is characterized in that compounds of the formulae (I-1-a) to (I-5-a) are reacted in each case with sulphonyl chlorides of the formula (XIII), if appropriate in the presence of a diluent and if appropriate in the presence of an acid binder.

In preparation process (I), approximately 1 mol of sulphonyl chloride of the formula (XIII) is reacted per mole of starting compound of the formulae (I-1-a) to (I-5-a) at −20 to 150° C., preferably at 0 to 70° C.

Process (I) is preferably carried out in the presence of a diluent.

Suitable diluents are all inert polar organic solvents such as ethers, amides, ketones, carboxylic esters, nitriles, sulphones, sulphoxides or halogenated hydrocarbons such as methylene chloride.

Dimethyl sulphoxide, tetrahydrofuran, dimethylformamide or methylene chloride are preferably employed.

If, in a preferred embodiment, the enolate salt of the compounds (I-1-a) to (I-5-a) is synthesized by adding strong deprotonating agents (such as, for example, sodium hydride or potassium tertiary-butylate), a further addition of acid binders can be dispensed with.

If acid binders are employed, then suitable substances are customary inorganic or organic bases, with sodium hydroxide, sodium carbonate, potassium carbonate, pyridine and triethylamine being mentioned by way of example.

The reaction can be carried out under atmospheric pressure or under elevated pressure, it is preferably carried out under atmospheric pressure. Working-up is carried out by customary methods.

Process (J) according to the invention is characterized in that compounds of the formulae (I-1-a) to (I-5-a) are reacted in each case with phosphorus compounds of the formula (XIV), if appropriate in the presence of a diluent and if appropriate in the presence of an acid-binding agent.

In preparation process (J), 1 to 2, preferably 1 to 1.3, mol of the phosphorus compound of the formula (XIV) are reacted at temperatures between −40° C. and 150° C., preferably between −10 and 110° C., to obtain compounds of the formulae (I-1-e) to (I-5-e).

Process (J) is preferably carried out in the presence of a diluent.

Suitable diluents are all inert polar organic solvents such as ethers, carboxylic esters, halogenated hydrocarbons, ketones, amides, nitrites, sulphones, sulphoxides and the like.

Substances which are preferably employed are acetonitrile, dimethyl sulphoxide, tetrahydrofuran, dimethylformamide or methylene chloride.

Suitable acid binders which are optionally added are customary inorganic or organic bases such as hydroxides, carbonates or amines. Examples which may be mentioned are sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods of organic chemistry. The end products are preferably purified by crystallization, chromatography or by so-called "incipient distillation", i.e. removal of the volatile components in vacuo.

Process (K) is characterized in that compounds of the formulae (I-1-a) to (I-5-a) are reacted in each case with metal hydroxides or metal alkoxides of the formula (XV), or amines of the formula (XVI), if appropriate in the presence of a diluent.

Diluents which can be employed in process (K) according to the invention are preferably ethers such as tetrahydrofuran, dioxane, diethyl ether, or else alcohols such as methanol, ethanol and isopropanol, but also water. Process (K) according to the invention is generally carried out under atmospheric pressure. The reaction temperature is generally between −20° C. and 100° C., preferably between 0° C. and 50° C.

Process (L) according to the invention is characterized in that compounds of the formulae (I-1-a) to (I-5-a) are reacted in each case with (Lα) compounds of the formula (XVII), if appropriate in the presence of a diluent and if appropriate in the presence of a catalyst, or (Lβ) with compounds of the formula (XVIII), if appropriate in the presence of a diluent and if appropriate in the presence of an acid-binding agent.

In preparation process (Lα), approximately 1 mol of isocyanate of the formula (XVII) is reacted at 0 to 100° C., preferably at 20 to 50° C., per mole of starting compound of the formulae (I-1-a) to (I-5-a).

Process (Lα) is preferably carried out in the presence of a diluent.

Suitable diluents are all inert organic solvents such as aromatic hydrocarbons, halogenated hydrocarbons, ethers, amides, nitrites, sulphones or sulphoxides.

If appropriate, catalysts can be added to accelerate the reaction. Very advantageous catalysts which can be employed are organotin compounds such as, for example, dibutyltin dilaurate.

The process is preferably carried out under atmospheric pressure.

In preparation process (Lβ), approximately 1 mol of carbamoyl chloride of the formula (XVIII) is reacted per mole of starting compound of the formulae (I-1-a) to (I-5-a) at 0 to 150° C., preferably at 20 to 70° C.

Suitable diluents which are optionally added are all inert polar organic solvents such as ethers, carboxylic esters, nitrites, ketones, amides, sulphones, sulphoxides or halogenated hydrocarbons.

Dimethyl sulphoxide, tetrahydrofuran, diemthylformamide or methylene chloride are preferably employed.

If, in a preferred embodiment, the enolate salt of the compounds (I-1-a) to (I-5-a) is synthesized by adding strong deprotonating agents (such as, for example, sodium hydride or potassium tertiary-butoxide), a further addition of acid binders can be dispensed with.

If acid binders are employed, then suitable substances are customary inorganic or organic bases, with sodium hydroxide, sodium carbonate, potassium carbonate, triethylamine and pyridine being mentioned by way of example.

The reaction can be carried out under atmospheric pressure or under elevated pressure, it is preferably carried out under atmospheric pressure. Working-up is carried out by customary methods.

The active compounds are suitable for controlling animal pests, preferably arthropods and nematodes, particularly insects and arachnids encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec..

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus, spp., *Pediculus humanus corporis,* Haematopinus spp. and Linognathus spp..

From the order of the Mallophaga, for example, Trichodectes spp. and Damalinea spp..

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphura padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp..

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp..

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds according to the invention are distinguished by a potent insecticidal and acaricidal activity.

They can be employed particularly successfully for controlling phytopathogenic insects, such as, for example, against the larvae of the mustard beetle (*Phaedon cochleariae*) or against the larvae of the green rice leafhopper (*Nephotettix cincticeps*) or against the caterpillars of the diamond-back moth (*Plutella maculipennis*).

The active compounds according to the invention can furthermore be used as defoliants, desiccants, haulm killers and, especially, as weedkillers. By weeds, in the broadest sense, these are to be understood all plants which grow in locations where they are undesired. Whether the substances according to the invention act as total or selective herbicides depends essentially on the amount used.

The dosage rates of the active compounds according to the invention, required for controlling weeds, are between 0.001 and 10 kg/ha, preferably between 0.005 and 5 kg/ha.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochonra, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The active compounds according to the invention are highly suitable for the selective control of monocotyledonous weeds in dicotyledonous crops pre- and post-emergence. For example, they can be employed very successfully for controlling grass weeds in cotton or sugar beet.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilants, acaricides, nematicides, fungicides, growth regulators or herbicides. The insecticides include, for example, phosphoric esters, carbamates, carboxylic esters, chlorinated hydrocarbons, phenylureas, substances produced by microorganisms, and the like.

Examples of particularly advantageous components and mixtures are the following:

Fungicides 2-aminobutane; 2-anilino-4-methyl-6-cyclopropylpyrimidine; 2',6'-dibromo-2-methyl-4'-trifluoromethoxy-4'- trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlarnide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalarn, copper sulphate and other copper preparations Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cylhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dirmethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formnothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amido-sulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide ranges. The active compound concentration of the use forms can be from 0.0000001 to 95% by weight of active compound, preferably from 0.0001 to 1% by weight.

They are used in a customary manner appropriate for the use forms.

When used against hygiene and stored-product pests, the active compound is distinguished by an outstanding residual action on wood and clay and by a good stability to alkali on limed substrates.

The active compounds according to the invention act not only against plant, hygiene and stored-product pests but also, in the veterinary medicine sector, against parasitic animals (ectoparasites) such as hard ticks, soft ticks, mange mites, Trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp..

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp..

From the order Diptera and the sub-orders Nematocerina and Brachycerina, for example, Aedes spp., Anopheles spp., Culex spp., Simulium spp., EusimuliurrL spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma, spp., Gasterophilus spp., Hippobosca spp., Lipoptena spp., Melophagus spp..

From the order of the Siphonapterida, for example, Pulex spp., Ctenocephalides spp., Xenopsylla spp., Ceratophyllus spp..

From the order of the Heteropterida, for example, Cimex spp., Triatoma spp., Rhodnius spp., Panstrongylus spp..

From the order of the Blattarida, for example, *Blatta orientalis, Periplaneta americana, Blattela germanica,* Supella spp..

From the sub-class of the Acaria (Acarida) and the orders of the Meta- and Mesostigmata, for example, Argas spp., Omithodorus spp., Otabius spp., Ixodes spp., Amblyomma spp., Boophilus spp., Dermacentor spp., Haemaphysatis spp., Hyalomma spp., Rhipicephalus spp., Dermanyssus spp., Raillietia spp., Pneumonyssus spp., Sternostoma spp., Varroa spp..

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp..

For example, they show outstanding activity against *Boophilus microplus* and *Lucilia cuprina.*

The active compounds according to the invention are also suitable for controlling arthropods which attack agricultural livestock such as, for example, cattle, sheep, goats, horses, pigs, donkeys, camels, buffaloes, rabbits, chickens, turkeys, ducks, geese, bees, other domestic animals such as, for example, dogs, cats, cage birds, aquarium fish, and so-called laboratory animals, such as, for example, hamsters, guinea pigs, rats and mice. By controlling these arthropods, it is intended to diminish cases of death and reductions in productivity (meat, milk, wool, hides, eggs, honey and the like), so that simpler and more economical animal keeping is possible by employing the active compounds according to the invention.

In the veterinary sector, the active compounds according to the invention are used in a known manner by enteral administration in the form of, for example, tablets, capsules, drinks, drenches, granules, pastes, boluses, the feed-through method, suppositories, by parenteral administration such as, for example, by injections (intramuscular, subcutaneous, intravenous, intraperitonial and the like), implants, by nasal administration, by dermal use in the form of, for example, bathing or dipping, spraying, pouring-on and spotting-on, washing, dusting, and with the aid of moulded articles comprising active compound, such as collars, ear marks, tail marks, limb bands, halters, marking devices and the like.

When used for livestock, poultry, domestic animals and the like, the active compounds of the formula (I) can be applied as formulations (for example powders, emulsions, flowables) which comprise the active compounds in an amount of 1 to 80% by weight, either directly or after dilution by a factor of 100 to 10,000, or they may be used as a chemical bath.

Moreover, it has been found that the compounds of the formula (I) according to the invention have a potent insecticidal activity against insects which destroy industrial materials.

The following insects may be mentioned by way of example and as being preferred, but without limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec., *Dinoderus minutus.*

Hymenoptera such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials such as, preferably, synthetic materials, glues, sizes, paper and board, leather, wood and derived timber products, and paints.

The material to be protected against attack by insects is very particularly preferably wood and derived timber products.

Wood and derived timber products which can be protected by the agent according to the invention, or by compositions comprising it, are to be understood as meaning, for example,: construction timber, wooden beams, railway sleepers, bridge components, jetties, wooden vehicles, boxes, pallets, containers, telephone poles, wood laggings, windows and doors made of wood, plywood, particle board, joiner's work, or wood products which, quite generally, are used in construction or in joinery.

The active compounds can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellent, if appropriate siccatives and UV stabilizers and, if appropriate, colorants and pigments and other processing auxiliaries.

The insecticidal compositions or concentrates used for the protection of wood and derived timber products comprise the active compound according to the invention, in a concentration of 0.0001 to 95% by weight, in particular 0.001 to 60% by weight.

The amount of the agents or concentrates employed depends on the species and the abundance of the insects and on the medium. The optimum amount used can be determined in each case by test series. However, in general it suffices to employ 0.0001 to 20% by weight, preferably 0.001 to 10% by weight, of the active compound based on the material to be protected.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

The organochemical solvents employed are preferably oily or oil-like solvents with an evaporation number of above 35 and a flashpoint of above 30° C., preferably above 45° C. Substances which are used as such oily and oil-type solvents of low volatility which are insoluble in water are suitable mineral oils or their aromatic fractions or mineral-oil-comprising solvent mixtures, preferably white spirit, petroleum and/or alkylbenzene.

It is advantageous to use mineral oils with a boiling range of 170 to 220° C., white spirit with a boiling range of 170 to 220° C., spindle oil with a boiling range of 250 to 350° C., petroleum or aromatics of a boiling range of 160 to 280° C., spirit of turpentine, and the like.

In a preferred embodiment, the substances used are liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene.

The organic oily or oil-type solvents of low volatility with an evaporation number of above 35 and a flashpoint of above 30° C., preferably above 45° C., can be replaced in part by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents containing hydroxyl and/or ester and/or ether groups, such as, for example, glycol ethers, esters and the like.

Organochemical binders which are used within the scope of the present invention are the binding drying oils and/or synthetic resins which are known per se, can be diluted with water, and/or are soluble, dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene-coumarone resin, silicone resin, drying vegetable and/or drying oils and/or physically drying binders based on natural and/or synthetic resin.

The synthetic resin used as binder can be employed in the form of an emulsion, dispersion or solution. Substances which can also be used as binders are bitumen or bituminous substances in amounts of up to 10% by weight. In addition, colorants, pigments, water repellants, odoriferous substances and inhibitors or anti-corrosives and the like, all of which are known per se, can be employed.

The composition or concentrate preferably comprises, in accordance with the invention, at least one alkyd resin or modified alkyd resin and/or a drying vegetable oil as the organochemical binder. Substances which are preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds or crystallization or precipitation. They preferably replace 0.01 to 30% of the binder (based on 100% of binder employed).

The plasticizers are from the chemical classes of the phthalic esters, such as di-butyl phthalate, dioctyl phthalate or benzylbutyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone or ethylenebenzophenone.

Another suitable solvent or diluent is, in particular, water, if appropriate in a mixture with one or more of the abovementioned organochemical solvents or diluents, emulsifiers and dispersants.

A particularly effective protection of wood is achieved by means of industrial-scale impregnating processes, for example vacuum, double-vacuum or pressure processes.

If appropriate, the ready-to-use compositions can comprise other insecticides and, if appropriate, one or more fungicides.

Additional components which may be admixed are preferably the insecticides and fungicides mentioned in WO 94/29 268. The compounds mentioned in this document are expressly part of the present application.

Components which may very particularly preferably be admixed are insecticides such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

Preparation and use of the active compounds according to the invention can be seen from the examples which follow.

Preparation Examples

Example (I-B-1-a-1)

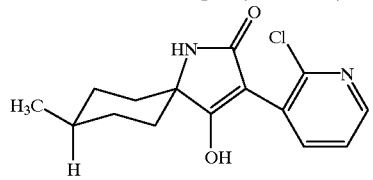

11.3 g of the compound of Example (II-B-1) in 22 ml of DMF are added dropwise at 0 to 10° C. to 8.82 g (0.075 mol) of potassium tert-butylate in 30 ml of DMF, and the mixture is stirred at room temperature. The progress of the reaction is monitored by means of thin-layer chromatography (TLC). When the reaction has ended, 250 ml of ice-water are added, the mixture is acidified with concentrated hydrochloric acid at 0 to 10° C. until the pH is 2 and subjected to filtration with suction, and the filtrate is washed with water, dried and brought to the boil with methyl tert-butyl ether (MTB ether)/n-hexane for purification.

Yield 7.90 g (77% of theory), m.p. >220° C.

The following compounds of the formula (I-1-a) were obtained analogously to Example I-B-1-a-1, or following the general information given for the preparation of the compounds of the formula (I-1-a):

Example (I-B-1-1)

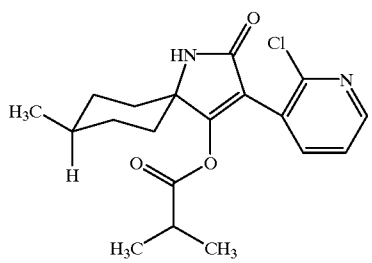

1.3 ml (0.012 mol) of isobutyryl chloride in 5 ml of anhydrous ethyl acetate are added dropwise at reflux temperature to 2.34 g of the compound of Example (I-B-1-a1) and 1.7 ml (12 mmol) of triethylamine in 50 ml of anhydrous ethyl acetate, the mixture is stirred under reflux, and the progress of the reaction is monitored by means of TLC. After the reaction has ended, the mixture is concentrated, taken up in methylene chloride, washed twice with 50 ml of 0.5 N NaOH, dried and concentrated. The residue is recrystallized from MTB ether/n-hexane.

Yield 1.5 g (51% of theory), m.p. 204° C.

The following compounds of the formula (I-1-b) were obtained analogously to Example I-B-1-b-1, or following the general information given for the preparation:

TABLE 40

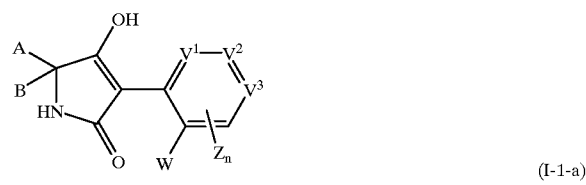

(I-1-a)

| Ex. No. | $V^1$ | $V^2$ | $V^3$ | W | $Z_n$ | A | B | Isomer | M.p. ° C. |
|---|---|---|---|---|---|---|---|---|---|
| I-B-1-a-2 | C—Cl | N | C—Cl | H | H | $CH_3$ | $CH_3$ | — | >220 |
| 1-B-1-a-3 | C—Cl | N | C—Cl | H | H | —$(CH_2)_2$—$CHCH_3$—$(CH_2)_2$— | | β | >220 |
| I-B-1-a-4 | C—H | N | C—Cl | Cl | H | —$(CH_2)_2$—$CHCH_3$—$(CH_2)_2$— | | β | >220 |
| I-B-1-a-5 | C—Cl | N | C—Cl | H | H | —$(CH_2)_2$—$CHOCH_3$—$(CH_2)_2$— | | β | >220 |

TABLE 41

(I-1-b)

| Ex. No. | $V^1$ | $V^2$ | $V^3$ | W | $Z_n$ | A | B | $R^1$ | Isomer | M.p. °C. |
|---|---|---|---|---|---|---|---|---|---|---|
| I-B-1-b-2 | C—Cl | N | C—Cl | H | H | $CH_3$ | $CH_3$ | i-$C_3H_7$ | — | 149 |
| I-B-1-b-3 | C—Cl | N | C—Cl | H | H | $CH_3$ | $CH_3$ | $C_2H_5$—O—$CH_2$ | — | 118 |
| I-B-1-b-4 | C—Cl | N | C—Cl | H | H | —$(CH_2)_2$—$CHCH_3$—$(CH_2)_2$— | | i-$C_3H_7$ | β | 204 |
| I-B-1-b-5 | C—Cl | N | C—Cl | H | H | —$(CH_2)_2$—$CHCH_3$—$(CH_2)_2$— | | $C_2H_5$—O—$CH_2$ | β | 190 |
| I-B-1-b-6 | C—Cl | N | C—Cl | H | H | —$(CH_2)_2$—$CHCH_3$—$(CH_2)_2$— | | 4-Cl-Phenyl | β | 232 |
| I-B-1-b-7 | C—Cl | N | C—Cl | H | H | —$(CH_2)_2$—$CHCH_3$—$(CH_2)_2$— | | 2-Thienyl | β | >220 |

Example (I-B-1-c-1)

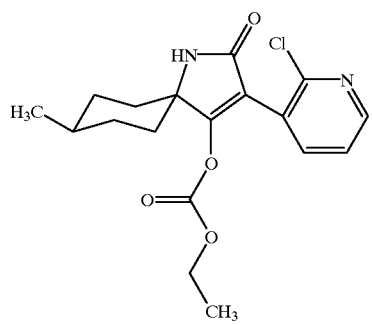

0.8 ml (0.008 mol) of ethyl chloroformate in 5 ml of anhydrous methylene chloride are added dropwise at 0 to 10° C. to 2.34 g of the compound of Example (I-B-1-a-1) and 1.2 ml (0.008 mol) of triethylamine in 50 ml of anhydrous methylene chloride. The mixture is stirred at room temperature and the progress of the reaction is monitored by means of TLC. After the reaction has ended, the mixture is washed twice with 50 ml of 0.5 N NaOH, dried and concentrated, and the residue is recrystallized from MTB ether/n-hexane. To purify the product further, it is boiled again in ethyl acetate.

Yield 1.6 g (54% of theory), m.p. 208° C.

The following compounds of the formula (I-1-c) were obtained analogously to Example I-B-1-c-1, or following the general information given for the preparation:

TABLE 42

(I-1-c)

| Ex. No. | $V^1$ | $V^2$ | $V^3$ | W | $Z_n$ | A | B | L | M | $R^2$ | M.p. °C. | Isomer |
|---|---|---|---|---|---|---|---|---|---|---|---|---|
| I-B-1-c-2 | C—Cl | N | C—Cl | H | H | $CH_3$ | $CH_3$ | O | O | $C_2H_5$ | 104 | — |
| I-B-1-c-3 | C—Cl | N | C—Cl | H | H | —$(CH_2)_2$—$CHCH_3$—$(CH_2)_2$— | | O | O | $C_2H_5$ | >220 | β |

Example (II-B-1)

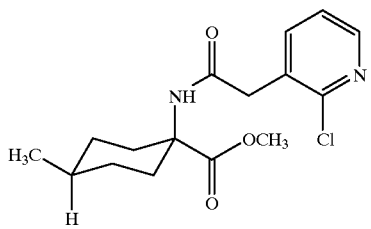

9.5 g of methyl cis-4-methyl-1-amino-cyclohexanecarboxylate hydrochloride and 12.8 ml of triethylamine are stirred for 5 minutes in 90 ml of anhydrous tetrahydrofuran (THF). After 7.8 g of 3-(2-chloro)-pyridylacetic acid have been added in accordance with Example (XXIII-B-1), the mixture is stirred for a further 15 minutes at room temperature, 17.8 ml (0.127 mol) of triethylamine are then added, and 4.3 ml of phosphorus oxychloride are immediately added in such a way that the solution is at a moderate boil. The mixture is then refluxed for 30 minutes. The mixture is poured into 400 ml of ice-water and extracted with methylene chloride, and the methylene chloride phase is dried and concentrated. The residue is purified by column chromatography on silica gel (eluent methylene chloride/ethyl acetate 3:1).

Yield 11.3 g (76% of theory), m.p. 124° C.

The following compounds of the formula (II) were obtained analogously to Example II-B-I, or following the general information given for the preparation:

added with cooling, 70.8 g of isopentyl nitrite in 240 ml of acetonitrile are then added dropwise at room temperature in the course of 5 minutes, and the mixture is subsequently stirred at room temperature until the evolution of gas has ceased. The mixture is then poured into 1600 ml of ice-cold 20% strength HCl and extracted repeatedly with methyl tert-butyl ether (MTB), and the organic phase is washed with 20% strength HCl, dried and concentrated.

Yield 165 g. The crude product is employed without further purification for the synthesis of the compound of Example (XXV-B-1).

Example (XXV-B-1)

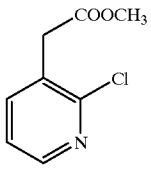

327 ml of 30% strength aqueous $NaHCO_3$ solution are added dropwise with cooling to 165 g of the crude compound of Example (XXV-B-1) in 150 ml of anhydrous methanol. The mixture is stirred for 5 hours under reflux, 48 ml of concentrated sulphuric acid are subsequently added dropwise at room temperature, and stirring is continued for 1 hour under reflux.

Excess methanol is removed in vacuo, the residue is extracted with methylene chloride, and the methylene chloride phase is dried and concentrated. The residue is distilled.

TABLE 43

(II)

| Ex. No. | $V^1$ | $V^2$ | $V^3$ | W | $Z_n$ | A | B | $R^8$ | M.p. ° C. | Isomer |
|---|---|---|---|---|---|---|---|---|---|---|
| II-B-2 | C—Cl | N | C—Cl | H | H | —$(CH_2)_2$—$CHCH_3$—$(CH_2)_2$— | | $CH_3$ | 146 | β |
| II-B-3 | C—Cl | N | C—Cl | H | H | $CH_3$ | $CH_3$ | $CH_3$ | 138 | — |
| II-B-4 | C—Cl | N | C—Cl | H | H | —$(CH_2)_2$—$CHOCH_3$—$(CH_2)_2$— | | $CH_3$ | 122 | β |
| II-B-5 | CH | N | C—Cl | Cl | H | —$(CH_2)_2$—$CHCH_3$—$(CH_2)_2$— | | $CH_3$ | 136 | β |
| II-B-6 | CH | N | C—Cl | Cl | H | $CH_3$ | $CH_3$ | $CH_3$ | 119 | — |
| II-B-7 | CH | N | C—Cl | Cl | H | —$(CH_2)_2$—$CHOCH_3$—$(CH_2)_2$— | | $CH_3$ | 137 | β |

Example (XXV-B-1)

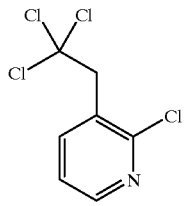

600 g (6.05 mol) of 1,1-dichloroethylene are added at room temperature in the course of 5 minutes to 50 g (0.39 mol) of 3-amino-2-chloropyridine in 120 ml of anhydrous acetonitrile, and stirring is continued for 5 minutes. 62.9 g (0.47 mol) of anhydrous $CuCl_2$ are subsequently rapidly Yield 13.1 g (18% of theory), b.p.: 110–115° C. at 0.150 mbar.

Example (XXIII-B-1)

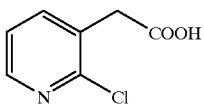

A solution of 4 g (0.095 mol) of lithium hydroxide (purity 98%) in 133 ml of water is added dropwise at room temperature to 13.1 g (0.077 mol) of the compound of Example (XXIV-B-1) (purity 90%) in 133 ml of anhydrous THF, and the mixture is stirred for one day at this temperature. The progress of the reaction is monitored by means of TLC and, if appropriate, more lithium hydroxide is added. The mixture is then concentrated, 50 ml of water are added, and the mixture is extracted with MTB ether. The aqueous phase is then acidified with 3N HCl and re-extracted with MTB ether. The aqueous phase is brought to pH 4–5. The product is filtered off with suction and dried.

Yield 7.6 g (51% of theory), m.p.: 197° C.

Example (XXIII-B-2)

(XXIII-B-2)

This compound was prepared by the following equation:

Compound (2)

1060 g of acrylonitrile (1) and 1120 g of DABCO are stirred for 60 hours at 70° C. The mixture is allowed to cool, 4 l of toluene and 5 l of water are added, and the organic phase is washed with 1 N HCl, dried and concentrated. The residue is distilled over a film evaporator at 0.5 mbar/150° C.

Yield: 380 g, b.p. 70 to 72° C./0.20 mbar.

Compound (3)

1113 g of chlorine are passed into a mixture of 500 g of compound (2), 250 g of carbon tetrachloride and 5.8 g of benzoyl peroxide at 70° C. Every hour, a further 5.8 g of benzoyl peroxide are added. The mixture is subsequently concentrated. The crude product is employed in the preparation of the compound (4) without further purification.

Yield: 862 g (Δ 79% of theory)

Compound (4)

309.1 g of compound (3), 950 ml of acetic acid and 221.3 g 78% strength sulphuric acid are refluxed for 2.5 hours. After cooling, the mixture is stirred into approx. 1800 ml of ice-water, stirred for 1.5 hours and filtered with suction. The crude product is stirred 2 more times with in each case 3.5 l of water, filtered off with suction, washed until neutral and dried at 50° C.

Yield: 64.3%, m.p. 131 to 132° C.

Compound (5)

220 g of compound (4) are heated with 1.2 l of $POCl_3$ for 3 hours at 160° C. under nitrogen pressure of 5 bar. Excess $POCl_3$ is distilled off, and the residue is stirred into ice, filtered with suction, washed thoroughly with water and dried at 40° C.

Yield: 68%, NMR (200 MHz, $CDCl_3$): δ=4.65 (s,2H, $CH_2$—Cl), 7.32 (d,1H, pyrid. 3-H), 7.83 (d,1H, pyrid. 6-H)

Compound (6)

A solution of 106 g (0.5 mol) of compound (5) (purity 94.5%) in 100 ml of toluene is slowly added dropwise at 60 to 80° C. to a mixture of 31 g (0.64 mol) of NaCN and 1 g of Aliquat 336 in 50 ml of water, and the mixture is stirred for 8 hours at 80° C. After 31 g of NaCN and 1 g of Aliquat 336 have been added, the mixture is stirred for a further 8 hours at 80° C. After cooling, in each case 100 ml of water and toluene are added, the organic phase is washed twice with in each case 300 ml of saturated aqueous NaCl solution, dried and concentrated, and the residue is distilled under a high vacuum.

Yield: 29%, m.p. 80 to 82° C.

Example (XXIII-B-2)

24.2 g (0.127 mol) of compound (6) are added at 80 to 90° C. to a mixture of 119.3 ml of concentrated sulphuric acid and 141.3 ml of water, and the mixture is stirred for 2 hours under reflux. After cooling, the mixture is poured into 500 ml of ice-water, filtered with suction, washed with ice-water until neutral and dried.

Yield: 74%, m.p. 134 to 135° C.

Example (XXIII-B-3)

This compound was prepared in accordance with the following equation:

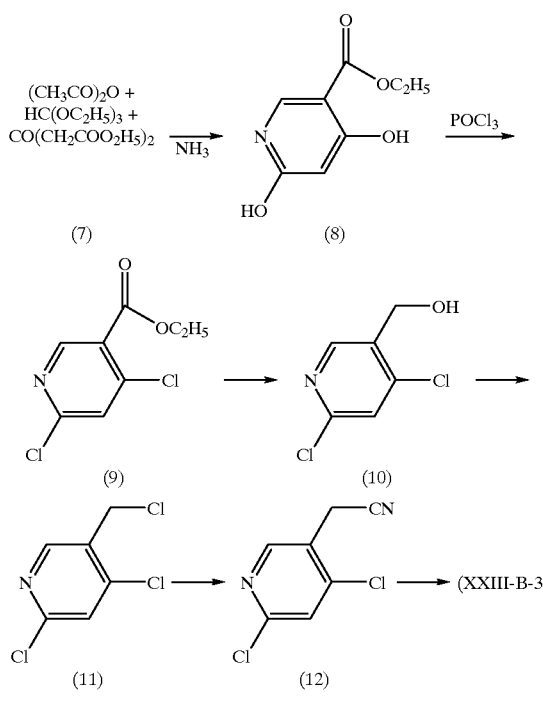

Compound (8)

249 g of diethyl acetonedicarboxylate (7), 233.4 g of acetic anhydride and 164.4 g of triethyl orthoformate are stirred for 1 hour at 140° C. All components which are volatile at up to 120° C. are distilled off and the mixture is cooled to room temperature. 450 ml of 25% strength $NH_3$ are subsequently added and the precipitate is filtered off with suction. It is suspended in water. The suspension is brought to pH 1 with concentrated HCl and filtered with suction, and the product is dried overnight. The crude product is boiled up in 1 l of toluene, filtered off with suction and dried.

Yield: 107.5 g (51% of theory), m.p. 214° C.

Compound (9)

11.0 g of compound (8) are refluxed for 7 hours in 67 ml of $POCl_3$. Most of the excess $POCl_3$ is distilled off, and the residue is poured onto ice-water. The mixture is brought to pH 5 by adding $Na_2CO_3$ and extracted with methylene chloride, and the methylene chloride phase is dried, concentrated and distilled.

Yield: 8.3 g (63% of theory), b.p. 83° C./0.3 mbar.

Compound (10)

8.6 g of lithium aluminium hydride are added, a little at a time, in the course of approximately 1 hour at 5 to 10° C. to 66.02 g of compound (9) in 120 ml of dry tetrahydrofuran (THF), and the mixture is stirred for another 2 hours at this temperature. Then, 250 ml of 3N HCl are added dropwise at 5 to 8° C., and the reaction mixture is evaporated to dryness. The mixture is extracted with $CH_2Cl_2$, dried, concentrated and purified by column chromatography with the eluent ethyl acetate/cyclohexane ½.

Yield: 32.9 g (61% of theory), m.p. 83° C.

Compound (11)

0.94 g of compound (10) is boiled under reflux for 19 hours together with 7 ml of $POCl_3$. After the excess $POCl_3$ has been distilled off, the residue is poured onto ice, and the crude product is filtered off with suction, washed with water and dried in the air.

Yield: 0.25 g (26% of theory), m.p. 53° C.

Compound (12)

9.8 g of KCN in 38 ml of water are added dropwise at room temperature to 10.27 g of compound (11) and 0.9 g of tetrabutylammonium sulphate in 50 ml of methylene chloride, and the mixture is stirred overnight at room temperature. The organic phase is then concentrated and the residue is chromatographed on silica gel using the eluent ethyl acetate/cyclohexane ½.

Yield: 6.0 g (63% of theory), m.p. 56° C.

(XXIII-B-3)

1 g of compound (12) is refluxed for 2 hours in 4.8 ml of concentrated sulphuric acid and 5.7 ml of water. When cold, the mixture is poured into 20 ml of ice-water and filtered with suction, and the product is washed to neutrality and dried.

Yield: 0.85 g (81% of theory), m.p. 145° C.

The compounds of Examples (XXIII-B-1), (XXIII-B-2) and (XXIII-B-3) may be converted into the corresponding acid chlorides in a generally known manner, for example also in situ (see Example II-B-1):

Example (XX-B-1)

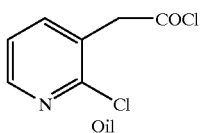

Oil

Example (XX-B-2)

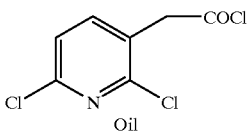

Oil

Example (XX-B-3)

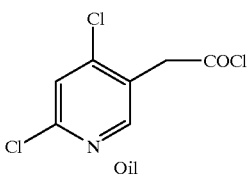

Oil

Example (I-B-2-a-1)

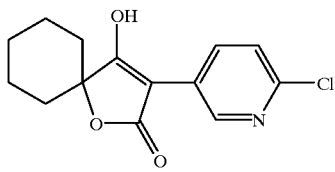

3.36 g (0.03 mol) of potassium tert-butoxide are added at 0 to 5° C. in the course of approximately 5 minutes to 9.8 g (0.03 mol) of the compound of Example (III-2) (purity 73%) in 60 ml of absolute dimethylformamide (DMF), and stirring is continued for 1 hour at this temperature. The reaction mixture is then poured into 8 ml of concentrated HCl in 180 ml of ice-water and stirred for 30 minutes. The product is filtered off with suction, washed with water and dried at 40° C.

Yield: 7.0 g, m.p. 241.5° C.

Example (I-B-2-a-2)

The following compound is obtained analogously to Example (I-B-2-a-1), or following the general information for the preparation of compounds of the formula (I-2-a):

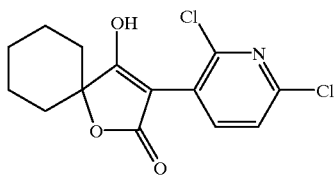

M.p. 195 to 198° C.

Example (I-B-2-b-1)

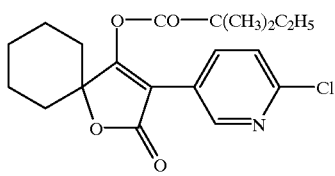

1.18 g (0.0088 mol) of 2,2-dimethylbutanoyl chloride in 5 ml of methylene chloride are added dropwise at 10 to 15° C. to 2.24 g (0.008 mol) of the compound of Example (I-B-2-a-1) and 1.0 g (0.01 mol) of triethylamine in 30 ml of methylene chloride, and the mixture is stirred overnight without cooling. 30 ml of methylene chloride are added, and the mixture is washed in succession with 50 ml of water, 50 ml of 10% strength aqueous sodium carbonate solution and 2 portions of 50 ml of water, dried and concentrated. The residue is stirred in petroleum ether, filtered off with suction and dried.

Yield: 1.2 g, m.p. 110° C.

Example (III-1)

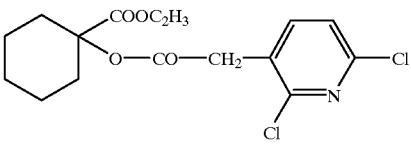

5.38 g of the compound of Example (XX-B-2) and 4.13 g of ethyl 1-hydroxycyclohexylcarboxylate are heated at 140° C. for a total of 14 hours, and the mixture is concentrated and degassed using an oil pump.

Yield: 8.3 g, oil.

Without further characterization, the product was converted into the compound of Example (I-B-2-a-2).

Example (III-2)

The compound

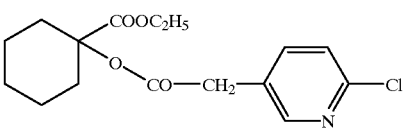

which was also converted directly into the compound of Example (I-B-2-a-1) without further characterization, was obtained analogously to Example (III-1), or following the general information given for the preparation of compounds of the formula (III).

USE EXAMPLES

Example 1

Tetranychus test (OP resistant/spray treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) which are severely infested with all development stages of the greenhouse red spider mite or two-spotted spider mite (*Tetranychus urticae*) are sprayed with an active compound preparation of the desired concentration.

After the desired period of time, the destruction in % is determined. 100% means that all the spider mites have been killed; 0% means that none of the spider mites have been killed.

In this test, an activity of 100% was shown, after 13 days, for example by the compound of Preparation Example (I-B-1-a-1) at an exemplary active compound concentration of 1000 ppm.

Example 2

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Rice seedlings (*Oryza sativa*) are treated by being dipped into the preparation of the active compound of the desired concentration and populated with the green rice leafhopper (Nephotettix cincticeps) while the leaves are still moist.

After the desired period of time, the destruction in % is determined. 100% means that all the leafhoppers have been killed; 0% means that none of the leafhoppers have been killed.

In this test, a destruction of 100% was caused, after 6 days, for example by the compounds of Preparation Examples (I-B-1-a-1), (I-B-1-b-1) and (I-B-1-c-1) at an exemplary active compound concentration of 0.1%.

What is claimed is:

1. A compound of the formula (I)

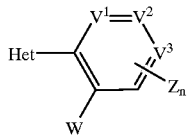

wherein
A) $V^1$ represents nitrogen and
   $V^2$ represents CH or C—Z and
   $V^3$ represents CY or
B) $V^1$ represents CX and
   $V^2$ represents nitrogen and
   $V^3$ represents CY or
C) $V^1$ represents CX and
   $V^2$ represents CH or C—Z and
   $V^3$ represents nitrogen
and wherein
W represents hydrogen, cyano, nitro, halogen, alkyl, alkenyl, alkynyl, alkoxy, alkylthio, halogenoalkyl, halogenoalkoxy, halogenoalkenyloxy, or in each case unsubstituted or substituted phenyl, phenoxy, phenylthio, phenylalkoxy or phenylalkylthio,
X represents hydrogen, halogen, alkyl, alkenyl, alkynyl, alkoxy, alkylthio, halogenoalkyl, halogenoalkoxy, halogenoalkenyloxy, cyano, nitro or in each case unsubstituted or substituted phenyl, phenoxy, phenylthio, phenylalkyloxy or phenylalkylthio,
Y represents hydrogen, halogen, alkyl, alkoxy, alkylthio, halogenoalkyl, halogenoalkoxy, cyano or nitro,
Z represents halogen, alkyl, alkoxy, alkylthio, halogenoalkyl, halogenoalkoxy, hydroxyl, cyano, nitro or in each case unsubstituted or substituted phenoxy, phenylthio, 5- or 6-membered hetaryloxy, 5- or 6-membered hetarylthio, phenylalkyloxy or phenylalkylthio, or
Y and Z together with the carbon atoms to which they are bonded represent an unsubstituted or substituted cycle which is uninterrupted or interrupted by hetero atoms, in which case n represents 1, or
W and Z together with the immediately adjacent carbon atoms to which they are bonded represent an unsubstituted or substituted cycle which is uninterrupted or interrupted by hetero atoms, in which case n represents 1,
n represents 0, 1 or, in the cases A) and C) 0, 1 or 2, wherein the substituents Z are identical or different when n=2, Het represents the group

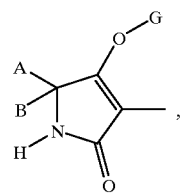

(1)

wherein
A represents hydrogen, or represents alkyl, alkenyl, alkoxyalkyl, polyalkoxyalkyl or alkylthioalkyl, each of which is unsubstituted or substituted by halogen, or represents in each case saturated or unsaturated and unsubstituted or substituted cycloalkyl or heterocyclyl, or represents aryl, arylalkyl or hetaryl, each of which is unsubstituted or substituted by halogen, alkyl, halogenoalkyl, alkoxy, halogenoalkoxy, cyano or nitro,
B represents hydrogen, alkyl or alkoxyalkyl, or
A and B together with the carbon atom to which they are bonded represent a saturated or unsaturated, unsubstituted or substituted carbocycle or heterocycle,
G represents hydrogen or is selected from the group consisting of

(b)

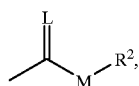

(c)

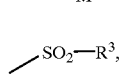

(d)

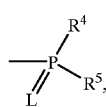

(e)

(f)

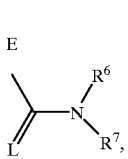

(g)

wherein
E represents a metal ion equivalent or an ammonium ion,
L represents oxygen or sulfur,
M represents oxygen or sulfur,
$R^1$ represents alkyl, alkenyl, alkoxyalkyl, alkylthioalkyl or polyalkoxyalkyl, each of which is unsubstituted or substituted by halogen, or represents cycloalkyl or heterocyclyl, each of which is unsubstituted or substituted by halogen, alkyl or alkoxy, or represents in each case unsubstituted or substituted phenyl, phenylalkyl, hetaryl, phenoxyalkyl or hetaryloxyalkyl,
$R^2$ represents alkyl, alkenyl, alkoxyalkyl or polyalkoxyalkyl, each of which is unsubstituted or substituted by halogen, or represents in each case unsubstituted or substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is unsubstituted or substituted by halogen, or represent in each case unsubstituted or substituted phenyl, benzyl, phenoxy or phenylthio, $R^6$ and $R^7$ independently of one another represent hydrogen, or represent alkyl, cycloalkyl, alkenyl, alkoxy or alkoxyalkyl, each of which is unsubstituted or substituted by halogen, or represent in each case unsubstituted or substituted phenyl or benzyl, or together with the N atom to which they are bonded form an unsubstituted or substituted cycle which optionally contains oxygen or sulfur.

2. A pesticide or a herbicide, comprising at least one compound of the formula (I) according to claim 1 and one or more extenders and/or surfactants.

3. A method of controlling pests or weeds, comprising the step of allowing a compound of the formula (I) according to claim 1 to act on pests or weeds, and/or their environment.

4. A process for preparing a pesticide or a herbicidal composition, comprising the step of mixing a compound of the formula (I) according to claim 1 with extenders and/or surfactants.

5. A process for preparing a compound of the formula (I-1-a)

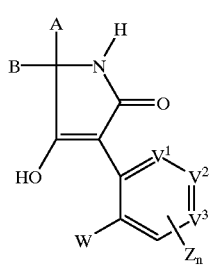

(I-1-a)

wherein

A, B, W, $V^1$, $V^2$, $V^3$, n and Z are as defined in claim 1, comprising the step of subjecting to an intramolecular condensation reaction a compound of the formula (II)

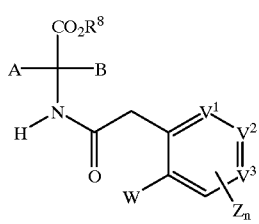

(II)

wherein

A, B, W, $V^1$, $V^2$, $V^3$, n and Z are as defined above and $R^8$ represents alkyl, in the presence of a diluent and in the presence of a base.

6. A compound of the formula (II)

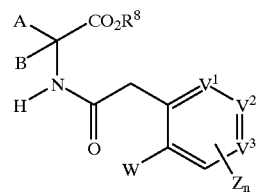

(II)

wherein

A represents alkyl, alkenyl, alkoxyalkyl, polyalkoxyalkyl or alkylthioalkyl, each of which is unsubstituted or substituted by halogen, or represents in each case saturated or unsaturated and unsubstituted or substituted cycloalkyl or heterocyclyl, or represents aryl, arylalkyl or hetaryl, each of which is unsubstituted or substituted by halogen, alkyl, halogenoalkyl, alkoxy, halogenoalkoxy, cyano or nitro, B represents alkyl or alkoxyalkyl, or A and B together with the carbon atom to which they are bonded represent a saturated or unsaturated, unsubstituted or substituted carbocycle or heterocycle, wherein A) $V^1$ represents nitrogen and
$V^2$ represents CH or C—Z and
$V^3$ represents CY or B) $V^1$ represents CX and
$V^2$ represents nitrogen and
$V^3$ represents CY or C) $V^1$ represents CX and
$V^2$ represents CH or C—Z and
$V^3$ represents nitrogen and wherein W represents hydrogen, cyano, nitro, halogen, alkyl, alkenyl, alkynyl, alkoxy, alkylthio, halogenoalkyl, halogenoalkoxy, halogenoalkenyloxy, or in each case unsubstituted or substituted phenyl, phenoxy, phenylthio, phenylalkoxy or phenylalkylthio, X represents hydrogen, halogen, alkyl, alkenyl, alkynyl, alkoxy, alkylthio, halogenoalkyl, halogenoalkoxy, halogenoalkenyloxy, cyano, nitro or in each case unsubstituted or substituted phenyl, phenoxy, phenylthio, phenylalkyloxy or phenylalkylthio, Y represents hydrogen, halogen, alkyl, alkoxy, alkylthio, halogenoalkyl, halogenoalkoxy, cyano or nitro, Z represents halogen, alkyl, alkoxy, alkylthio, halogenoalkyl, halogenoalkoxy, hydroxyl, cyano, nitro or in each case unsubstituted or substituted phenoxy, phenylthio, 5- or 6-membered hetaryloxy, 5- or 6-membered hetarylthio, phenylalkyloxy or phenylalkylthio, or Y and Z together with the carbon atoms to which they are bonded represent an unsubstituted or substituted cycle which is uninterrupted or interrupted by hetero atoms, in which case n represents 1, or W and Z together with the immediately adjacent carbon atoms to which they are bonded represent an unsubstituted or substituted cycle which is uninterrupted or interrupted by hetero atoms, in which case n represents 1, n represents 0, 1 or, in the cases A) and C) 0, 1 or 2, wherein the substituents Z are identical or different when n=2, and $R^8$ represents alkyl.

7. A compound of the formula (XXI)

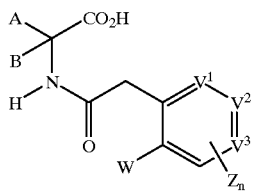

(XXI)

wherein

A represents alkyl, alkenyl, alkoxyalkyl, polyalkoxyalkyl or alkylthioalkyl, each of which is unsubstituted or substituted by halogen, or represents in each case saturated or unsaturated and unsubstituted or substituted cycloalkyl or heterocyclyl, or represents aryl, arylalkyl or hetaryl, each of which is unsubstituted or substituted by halogen, alkyl, halogenoalkyl, alkoxy, halogenoalkoxy, cyano or nitro, B represents alkyl or alkoxyalkyl, or A and B together with the carbon atom to which they are bonded represent a saturated or unsaturated, unsubstituted or substituted carbocycle or heterocycle, wherein
- A) $V^1$ represents nitrogen and
  $V^2$ represents CH or C—Z and
  $V^3$ represents CY or
- B) $V^1$ represents CX and
  $V^2$ represents nitrogen and
  $V^3$ represents CY or
- C) $V^1$ represents CX and
  $V^2$ represents CH or C—Z and
  $V^3$ represents nitrogen and wherein W represents hydrogen, cyano, nitro, halogens alkyl, alkenyl, alkynyl, alkoxy, alkylthio, halogenoalkyl, halogenoalkoxy, halogenoalkenyloxy, or in each case unsubstituted or substituted phenyl, phenoxy, phenylthio, phenylalkoxy or phenylalkylthio, X represents hydrogen, halogen, alkyl, alkenyl, alkynyl, alkoxy, alkylthio, halogenoalkyl, halogenoalkoxy, halogenoalkenyloxy, cyano, nitro or in each case unsubstituted or substituted phenyl, phenoxy, phenylthio, phenylalkyloxy or phenylalkylthio, Y represents hydrogen, halogen, alkyl, alkoxy, alkylthio, halogenoalkyl, halogenoalkoxy, cyano or nitro, Z represents halogen, alkyl, alkoxy, alkylthio, halogenoalkyl, halogenoalkoxy, hydroxyl, cyano, nitro or in each case unsubstituted or substituted phenoxy, phenylthio, 5- or 6-membered hetaryloxy, 5- or 6-membered hetarylthio, phenylalkyloxy or phenylalkylthio, or Y and Z together with the carbon atoms to which they are bonded represent an unsubstituted or substituted cycle which is uninterrupted or interrupted by hetero atoms, in which case n represents 1, or W and Z together with the immediately adjacent carbon atoms to which they are bonded represent an unsubstituted or substituted cycle which is uninterrupted or interrupted by hetero atoms, in which case n represents 1, n represents 0, 1 or, in the cases A) and C) 0, 1 or 2, wherein the substituents Z are identical or different when n=2.

* * * * *